US011051785B2

(12) United States Patent
Matsumoto et al.

(10) Patent No.: US 11,051,785 B2
(45) Date of Patent: Jul. 6, 2021

(54) HEARTBEAT DETECTION DEVICE AND HEARTBEAT DETECTION METHOD

(71) Applicant: Panasonic Intellectual Property Management Co., Ltd., Osaka (JP)

(72) Inventors: Yusuke Matsumoto, Osaka (JP); Suguru Nakao, Hyogo (JP); Hiroshi Kunimoto, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 91 days.

(21) Appl. No.: 16/356,519

(22) Filed: Mar. 18, 2019

(65) Prior Publication Data

US 2019/0282197 A1    Sep. 19, 2019

(30) Foreign Application Priority Data

Mar. 19, 2018   (JP) .............................. JP2018-050833
Mar. 19, 2018   (JP) .............................. JP2018-051648

(51) Int. Cl.
*A61B 5/00*   (2006.01)
*A61B 7/04*   (2006.01)
(Continued)

(52) U.S. Cl.
CPC ............ *A61B 7/04* (2013.01); *A61B 5/02444* (2013.01); *A61B 5/6803* (2013.01); *H04R 1/222* (2013.01);
(Continued)

(58) Field of Classification Search
CPC .......... A61B 7/04; A61B 5/024–02444; A61B 5/6803; A61B 2562/0204; A61B 2503/20; H04R 1/222; H04R 17/02; H04R 1/46; H04R 3/04; H04R 2460/13; H04R 5/033; H04R 1/1091; H04R 2201/107
See application file for complete search history.

(56) References Cited

U.S. PATENT DOCUMENTS

2013/0197377 A1   8/2013   Kishi et al.
2014/0114201 A1   4/2014   Watanabe et al.
(Continued)

FOREIGN PATENT DOCUMENTS

JP   58-153490   9/1983
JP   58-182397   10/1983
(Continued)

*Primary Examiner* — Scott M. Getzow
(74) *Attorney, Agent, or Firm* — Wenderoth, Lind & Ponack, L.L.P.

(57) ABSTRACT

A heartbeat detection device includes a bone conduction microphone that converts, into a signal, displacement on the body surface of a user in a thickness direction of the body of the user, and an extractor that extracts a first frequency component and a second frequency component which are included in the signal. The first frequency component is based on audio information of the user, and the second frequency component is based on heartbeat information of the user. The heartbeat detection device is capable of estimating the physical and psychological state of the user based on the heartbeat information by extracting both the audio information and the heartbeat information, from a signal that has been output by the bone conduction microphone.

16 Claims, 15 Drawing Sheets

(51) Int. Cl.
*A61B 5/024* (2006.01)
*H04R 1/22* (2006.01)
*H04R 17/02* (2006.01)
*H04R 1/46* (2006.01)
*H04R 3/04* (2006.01)

(52) U.S. Cl.
CPC ................ *H04R 1/46* (2013.01); *H04R 3/04* (2013.01); *H04R 17/02* (2013.01); *A61B 2562/0204* (2013.01)

(56) References Cited

U.S. PATENT DOCUMENTS

| | | |
|---|---|---|
| 2015/0119758 A1 | 4/2015 | Rogers et al. |
| 2016/0073966 A1* | 3/2016 | Lin ...................... A61B 5/7207 600/528 |
| 2018/0113673 A1* | 4/2018 | Sheynblat ............ H04R 1/1016 |

FOREIGN PATENT DOCUMENTS

| | | |
|---|---|---|
| JP | 6-54387 | 2/1994 |
| JP | 7-116138 | 5/1995 |
| JP | 2002-65650 | 3/2002 |
| JP | 2005-57737 | 3/2005 |
| JP | 2009-188638 | 8/2009 |
| JP | 2011-169697 | 9/2011 |
| JP | 2013-153782 | 8/2013 |
| JP | 2014-83122 | 5/2014 |
| JP | 2015-521062 | 7/2015 |
| JP | 2017-92906 | 5/2017 |
| WO | 2013/170018 | 11/2013 |

\* cited by examiner

HEARTBEAT DETECTION DEVICE AND HEARTBEAT DETECTION METHOD

CROSS REFERENCE TO RELATED APPLICATIONS

This application claims the benefit of priority of Japanese Patent Application Number 2018-051648 filed on Mar. 19, 2018 and Number 2018-050833 filed on Mar. 19, 2018, the entire contents of which are hereby incorporated by reference.

BACKGROUND

1. Technical Field

The present disclosure relates to a heartbeat detection device and a heartbeat detection method for extracting audio information and heartbeat information.

2. Description of the Related Art

In loud environments such as a construction site, a bone conduction microphone that obtains vocal cord vibrations propagating through bones is used to eliminate the influence of noise and obtain user's voice. A conventional bone conduction microphone is pressed, for use, against a portion where a flesh is thin and a bone such as a pharyngeal cartilage is just beneath the body surface (see, for example, Japanese Unexamined Patent Application Publication No. H6-54387 (Patent Literature (PTL) 1).

Heartbeat information is frequently used for the evaluation of a person's stress caused by a physical and psychological burden. Based on the fact that heartbeats reflect the activity of an autonomic nervous system, there is provided, for example, a device that calculates the fluctuations of a heart rate and of heartbeat intervals of a user based on heartbeat information, and determines the degree of user's fatigue based on the presence/absence of an instant increase in the resulting heart rate and a tendency observed in the temporal transition of the fluctuations in the resulting heartbeat intervals (see Japanese Unexamined Patent Application Publication No. 2002-65650 (Patent Literature (PTL) 2).

SUMMARY

What is concerned is that a worker who uses a bone conduction microphone in loud working environments has a great amount of physical and psychological stress. The present disclosure provides a heartbeat detection device and a heartbeat detection method for managing the physical and psychological state of a user who works under such environments, just by his/her carrying, on the body, a device for obtaining audio information.

A heartbeat detection device according to the present disclosure includes: a bone conduction microphone that converts, into a first signal, displacement on a body surface of a user in a thickness direction of a body of the user; and an extractor that extracts a first frequency component and a second frequency component which are included in the first signal. The first frequency component is based on audio information of the user, and the second frequency component is based on heartbeat information of the user.

A heartbeat detection method according to the present disclosure includes: placing a bone conduction microphone in contact with a surface body of a user; converting, into a first signal, displacement on the body surface in a thickness direction of a body of the user; and extracting a first frequency component and a second frequency component which are included in the first signal. The first frequency component is based on audio information of the user, and the second frequency component is based on heartbeat information of the user.

With the heartbeat detection device according to the present disclosure and the related technologies, it is possible to estimate the physical and psychological state of a user just by his/her carrying, on the body, a device for obtaining audio information.

BRIEF DESCRIPTION OF DRAWINGS

These and other objects, advantages and features of the disclosure will become apparent from the following description thereof taken in conjunction with the accompanying drawings that illustrate a specific embodiment of the present disclosure.

DETAILED DESCRIPTION OF THE EMBODIMENTS

A heartbeat detection device according to the present invention is used, for example, in loud environments such as a construction site, and obtains displacement on the body surface of a user. In addition, the heartbeat detection device extracts heartbeat information and audio information that propagate through the body of the user and are included in the obtained displacement. The audio information is information indicating a change in waveforms that vary based on the utterances of the user. The heartbeat information is information indicating a change in waveforms that vary based on the cardiac pulsation of the user.

The following describes in detail the embodiments according to the present disclosure with reference to the drawings. Note, however, that a description that is in detail but to the extent more than required is omitted in some cases. For example, a detailed description of a well-known matter and a duplicate description of substantially same elements are omitted in some cases. This aims to prevent the following description from being unnecessarily redundant and thus facilitate the understanding of the present disclosure by a person skilled in the art. Note that the attached drawings and the following description are provided for the person skilled in the art to thoroughly understand the present disclosure, and are not intended to limit the subject matters recited in the scope of the claims.

Embodiment 1

Heartbeat detection device 1 according to this embodiment has bone conduction microphone 3 and extracts audio information and heartbeat information that are included in displacement on the body surface of user U, which is obtained by bone conduction microphone 3.

1-1. Overall Configuration of Heartbeat Detection Device

Figure 1:
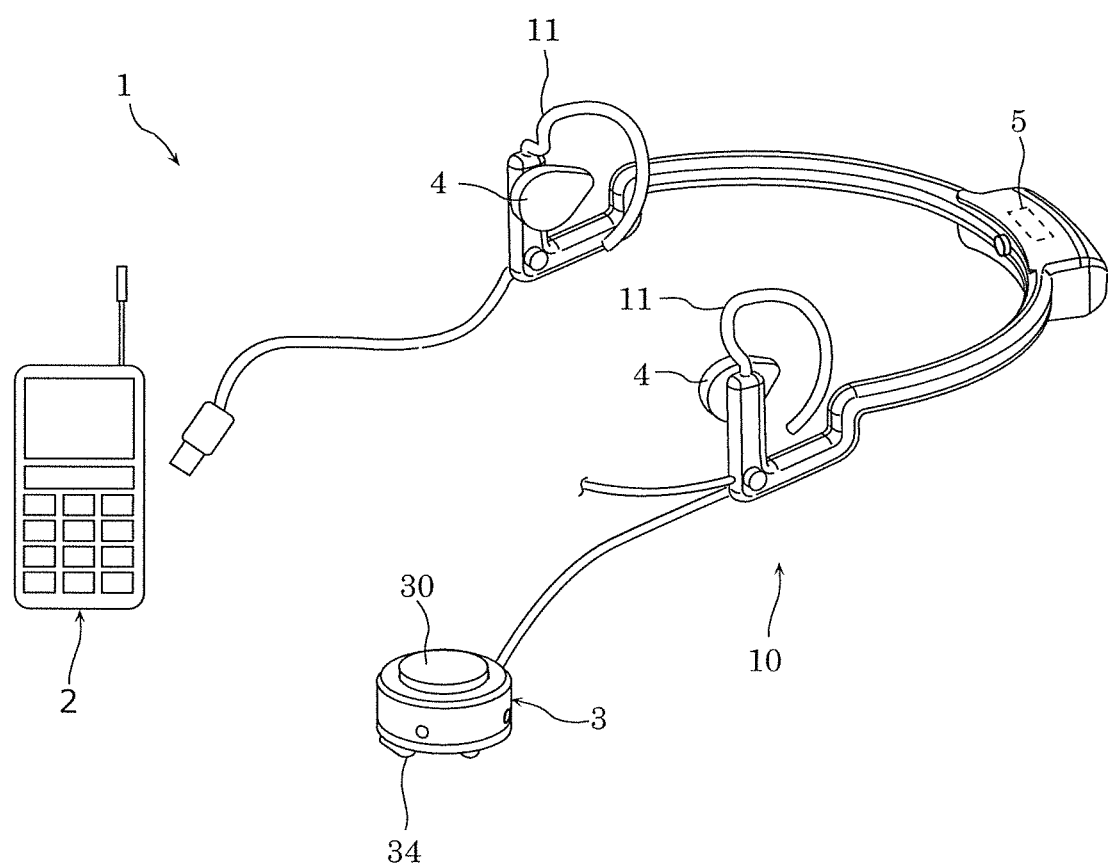
FIG. 1 is a perspective view illustrating a heartbeat detection device according to Embodiment 1.
Figure 2:
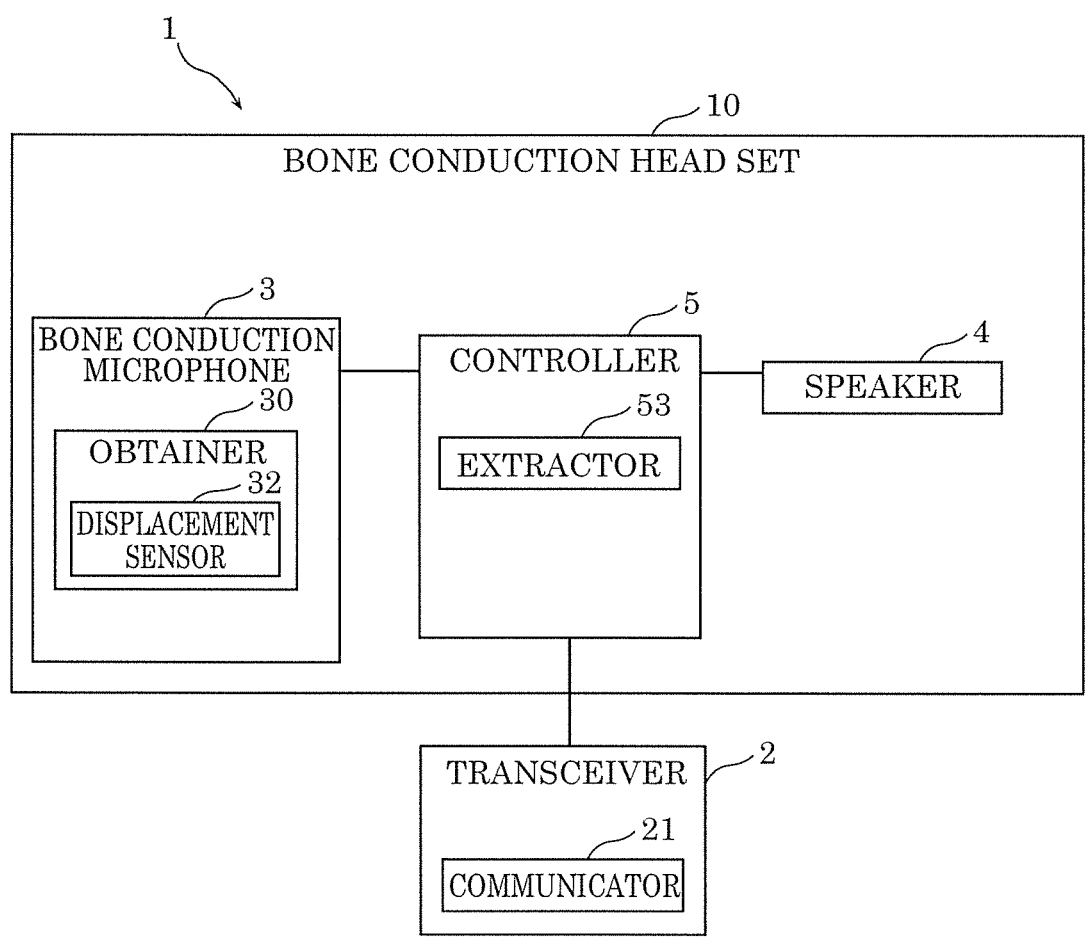
FIG. 2 is a schematic view illustrating a control configuration of the heartbeat detection device according to Embodiment 1.
Figure 3:
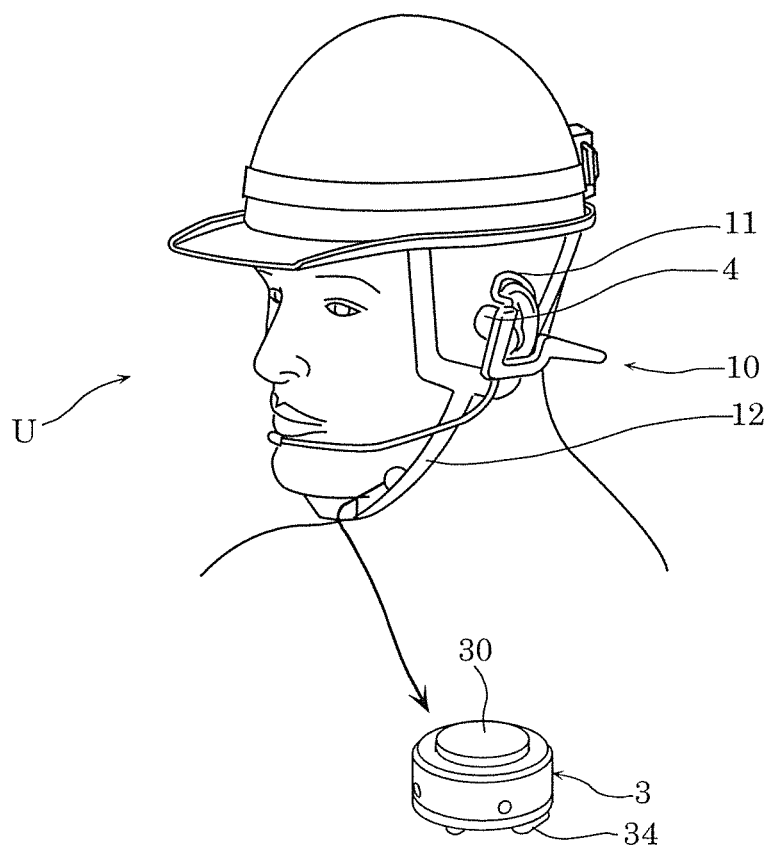
FIG. 3 is a perspective view illustrating how to wear a bone conduction head set according to Embodiment 1.

FIG. 1 is a perspective view illustrating heartbeat detection device 1 according to Embodiment 1. FIG. 2 is a schematic view illustrating a control configuration of heartbeat detection device 1 according to Embodiment 1. FIG. 3 is a view illustrating how to wear bone conduction head set 10 according to Embodiment 1.

As illustrated in FIG. 1 and FIG. 2, heartbeat detection device 1 includes bone conduction head set 10 and transceiver 2. Bone conduction head set 10 includes bone conduction microphone 3, speaker 4, and controller 5.
Transceiver 2 Includes Communicator 21.

Bone conduction microphone 3 is placed in contact with the surface body of user U, and obtains displacement on the body surface of user U. Bone conduction microphone 3 is a microphone produced with the aim primarily to obtain audio information that propagates through bones. It is therefore suitable to place bone conduction microphone 3 in contact with the body surface above bone (a solid portion where a bone such as a jawbone or a cheekbone is located just beneath a body surface). It is, however, considered that heartbeat information is transmitted mainly through soft tissues such as muscles, blood vessels, and fat. Placing bone conduction microphone 3 above bone lowers the level of obtaining heartbeat information, and thus, it is difficult to obtain heartbeat information at an extractable level. When both audio information and heartbeat information are to be obtained, as is the case of this embodiment, it is desirable to place bone conduction microphone 3 above soft tissues (a soft portion where soft tissues between a body surface and a bone is thick), and in particular, to place bone conduction microphone 3 in contact with the body surface of user U so that at least part of bone conduction microphone 3 contacts a portion of the body surface above a carotid artery, as illustrated in FIG. 3. The word "above" here in "above bone", "above soft tissues", and "above a carotid artery" means being on the side of the body surface of user U in the thickness direction (Z direction) of the body of user U. The level of obtaining audio information above soft tissues is lower than the case of obtaining audio information above bone. Audio information, however, is less position dependent than heartbeat information. It is therefore possible to obtain audible audio information even when bone conduction microphone 3 is placed in contact with the body surface above a carotid artery. Thus, user U is able to obtain both audio information and heartbeat information just by carrying one sensor on the body.

As illustrated in FIG. 3, bone conduction microphone 3 is attached to mounting fixture 12 by using clasp 34. Mounting fixture 12 causes obtainer 30 in bone conduction microphone 3 to press against the body surface of user U. This reduces the risk of changing the position at which bone conduction microphone 3 is placed and thus stabilizes the signal level of an obtained signal. It is desirable that mounting fixture 12 cause obtainer 30 in bone conduction microphone 3 to press against the body surface of user U with pressure in the range from 200 gram-force to 500 gram-force. When the pressure is weak, a thorough contact between obtainer 30 and the body surface of user U is insufficient and it is hard to obtain necessary information. In contrast, when the pressure is strong, an SN ratio between heartbeat information and noise is lowered, and thus, it is hard to obtain heartbeat information. In addition, pressing the body surface with strong pressure might cause the feeling of discomfort in user U. Since an optimal strength of pressure differs from person to person, it is desirable to determine the strength of pressure by appropriately adjusting the strength in the range from 200 gram-force to 500 gram-force.

It should be noted that in this embodiment, mounting fixture 12 is provided in the form of a chin strap in order to place bone conduction microphone 3 in contact with the body surface of user U above a carotid artery, but bone conduction microphone 3 may be placed in contact with the body surface using a tape unless bone conduction microphone 3 falls off the body surface or moves from the initial position.

Speaker 4 is, for example, a bone conduction speaker. As illustrated in FIG. 1, speaker 4 is held by holder 11. Speaker 4 is connected to controller 5 in a wired or wireless manner. Controller 5 is, for example, a central processing unit (CPU), a random access memory (RAM), or a read only memory (ROM). It should be noted that controller 5 may be, for example, a field-programmable gate array (FPGA), an application specific integrated circuit (ASIC), a microprocessor, an analog circuit, etc.

As illustrated in FIG. 2, communicator 21 is connected to controller 5 of bone conduction head set 10 in a wired or wireless manner. Communicator 21 then communicates with an external device. Specifically, communicator 21 receives, via controller 5, an input of a signal that has been output by bone conduction microphone 3, and transmits the signal to the external device. Communicator 21 also receives a signal transmitted by the external device and outputs the signal to speaker 4 via controller 5.

The external device with which communicator 21 communicates is, for example, an intercommunication device on the other end of communication via voice, or an information processing device. The information processing device is, for example, heartbeat detection device 1B to be described later, and is a personal computer that performs processing or monitoring of heartbeat information. Transceiver 2 is, for example, attached to a portion of clothes the user wears and is thus carried for use. Note that heartbeat detection device 1 may not include transceiver 2, and instead, bone conduction head set 10 may include communicator 21.

1-2. Configuration of Bone Conduction Microphone

Figure 4:
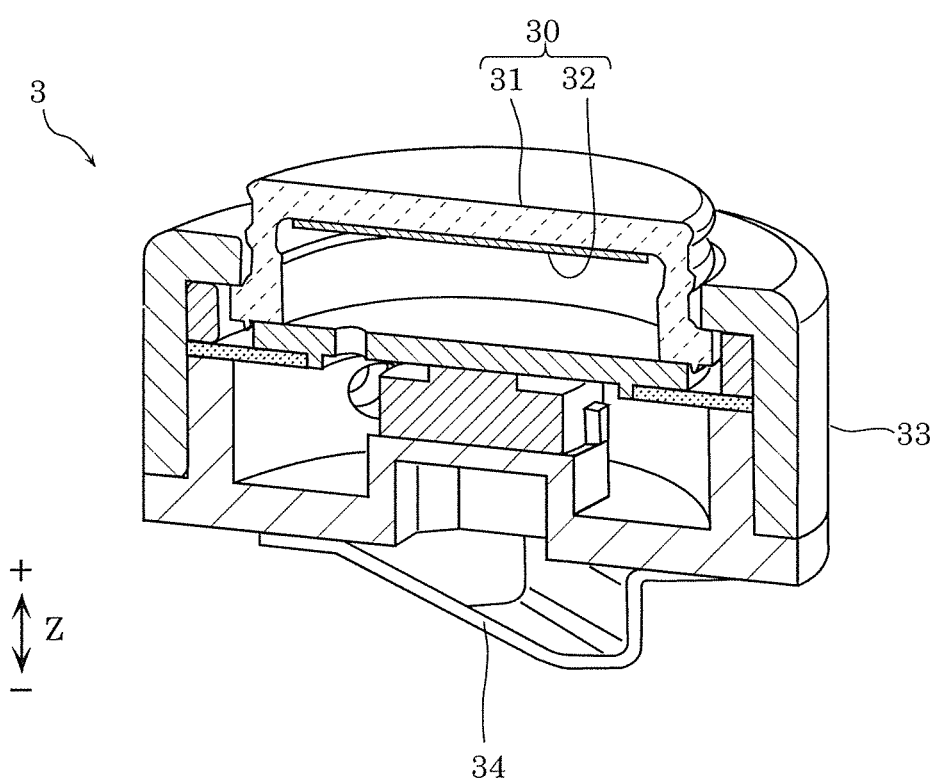
FIG. 4 is a cross-sectional perspective view illustrating a bone conduction microphone according to Embodiment 1.

Next, a configuration of bone conduction microphone 3 will be described in detail. FIG. 4 is a cross-sectional perspective view of the bone conduction microphone according to Embodiment 1.

As illustrated in FIG. 4, bone conduction microphone 3 includes obtainer 30 and casing 33. Obtainer 30 includes contacting component 31 that contacts the body surface of user U and displacement sensor 32 held by contacting component 31.

Contacting component 31 contacts the body surface of user U, obtains displacement on the body surface, and transmits the obtained displacement to displacement sensor 32. Contacting component 31 has an elastic body softer than casing 33, and is formed using, for example, a resin material such as silicon rubber. The meaning of being soft here includes both using a soft material and having a flexible structure (e.g., a form is easily changeable as a result of thin or wave-like formation). It is desirable that a material comfortable to the touch be used for contacting component 31.

Displacement sensor 32 is a detection element that detects displacement in a predetermined direction (Z direction, i.e., the thickness direction of a body) among displacements on the body surface of user U which are obtained via contacting component 31. Displacement sensor 32 converts the detected displacement on the surface body in the Z direction into an electric signal (the first signal), and inputs the electric signal to controller 5 in bone conduction head set 10. Displacement sensor 32 is attached on the inner wall of contacting component 31 so that displacement sensor 32 bends in the Z direction and thus produces thickness vibration. Since displacement sensor 32 is held by casing 33 via contacting component 31 that has an elastic body softer than casing 33, it becomes difficult to enter displacement sensor 32 for both vibration noise transmitted to casing 33 from outside and vibration noise caused inside casing 33. This allows bone conduction microphone 3 to easily obtain both audio information and heartbeat information that propagate through a body.

In this embodiment, displacement sensor 32 is a piezoelectric element having a flat-plate form that carries out thickness vibration. Displacement sensor 32 may be a capacitor that detects displacement on a body surface based on a change in capacity between two electrodes. In the case where heartbeat information indicating heartbeat at the time when user U utters is obtained using a piezoelectric element, it is possible to obtain the heartbeat information with a higher level of an SN ratio between heartbeat information and noise, compared to the case of using a capacitor. It is therefore easier, with a piezoelectric element, to obtain a signal from which both heartbeat information and audio information are extractable at the same time.

Casing 33 holds obtainer 30.

1-3. Extraction of Audio Information and Heartbeat Information

Figure 5:
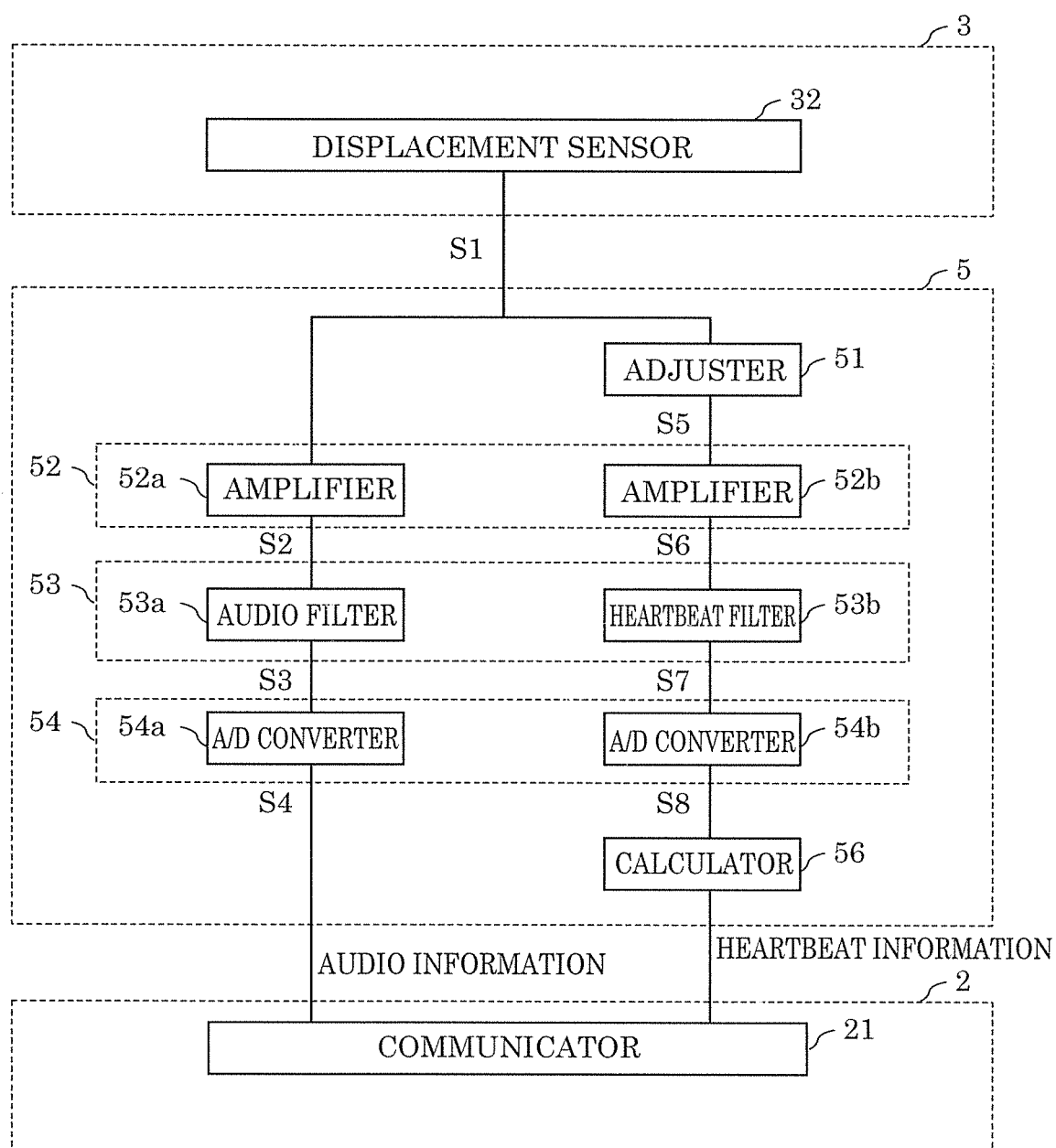
FIG. 5 is a block diagram illustrating in detail the control configuration according to Embodiment 1.

FIG. 5 is a block diagram illustrating a control configuration according to Embodiment 1.

First, displacement sensor 32 in bone conduction microphone 3 converts, into signal S1 that is analog data, displacement on the body surface of user U in a Z direction.

Controller 5 detects audio information and heartbeat information included in signal S1. As illustrated in FIG. 5, controller 5 includes adjuster 51, amplifier 52, extractor 53, A/D converter 54, and calculator 56. Audio information will be described first.

Amplifier 52a in amplifier 52 amplifies signal S1 and outputs signal S2 that has been amplified. Amplifier 52a determines an amplification factor based on the signal level of audio information, and carries out amplification a constant amplification factor.

Audio filter 53a (the first extractor) in extractor 53 extracts a frequency component (the first frequency component) that is based on audio information and is included in signal S2. Audio information mainly has a frequency component higher than 100 Hz whereas heartbeat information mainly has a frequency component less than 10 Hz. In view of this, a high pass filter (HPF) that eliminates a frequency bandwidth lower than or equal to 100 Hz is used for audio filter 53a in this embodiment. It should be noted that controller 5 may not include audio filter 53a, but it is desirable to provide controller 5 with audio filter 53a in the case where bone conduction microphone 3 is placed in contact with the surface body of user U above a carotid artery because heartbeat information overlaps with audio information.

A/D converter 54a in A/D converter 54 converts signal S3 that is analog data into signal S4 that is digital data.

Communicator 21 in transceiver 2 transmits, to an external device, signal S4 (audio information) that is output by controller 5. The external device is, for example, an intercommunication device on the other end of communication via voice.

Next, heartbeat information will be described.

Adjuster 51 receives an input of signal S1, adjusts the output position of signal S1 by eliminating the DC offset of signal S1 and outputs signal S5 whose output position has been adjusted. DC offset is an amount of difference between a DC component in signal S1 to be input and a zero reference value of an output of A/D converter 54b. A central value in the range of input values from A/D converter 54b is usually applied to the zero reference value, but the zero reference value shall not be restricted to such. It is preferable that the zero reference value be set in such a range that the saturation of values indicating the waveform of signal S7 to be input to A/D converter 54b is avoided. Adjuster 51 eliminates the influence caused by an individual difference among bone conduction microphones 3 to be used and the surrounding environment of bone conduction microphone 3. In addition, adjuster 51 makes it easier to extract heartbeat information having a low signal level.

Amplifier unit 52b in amplifier 52 amplifies signal S5 and outputs signal S6 that has been amplified. Amplifier unit 52b determines an amplification factor based on the signal level of heartbeat information, and carries out amplification with a constant amplification factor.

Heartbeat filter 53b (the second extractor) in extractor 53 extracts a frequency component (the second frequency component) that is based on heartbeat information and is included in signal S6, and outputs signal S7. In this embodiment, a low pass filter (LPF) that eliminates a frequency bandwidth higher than or equal to 10 Hz is used for heartbeat filter 53b.

It should be noted that a band pass filter (BPF) that allows a predetermined bandwidth to pass may be used for aforementioned audio filter 53a and heartbeat filter 53b.

A/D converter 54b in A/D converter 54 converts signal S7 that is analog data into signal S8 that is digital data.

Calculator 56 receives an input of signal S8 and performs analysis processing of heartbeat information. Calculator 56 calculates a cardiac cycle of user U. A cardiac cycle is used, for example, for calculating a heart rate or heartbeat fluctuations, and is useful for knowing the stressful state of user U. An example of calculator 56 will be described in detail in Embodiment 3.

Communicator 21 in transceiver 2 transmits, to an external device, the output of calculator 56 (e.g., data indicating cardiac cycle, heart rate, and heartbeat fluctuations). The external device is, for example, an information processing device such as a personal computer. The external device, for example, displays or further analyzes the transmitted data. It should be noted that communicator 21 may transmit the heartbeat information extracted by heartbeat filter 53b to the external device. In that case, the external device may analyze the heartbeat information received, etc.

Figure 6:
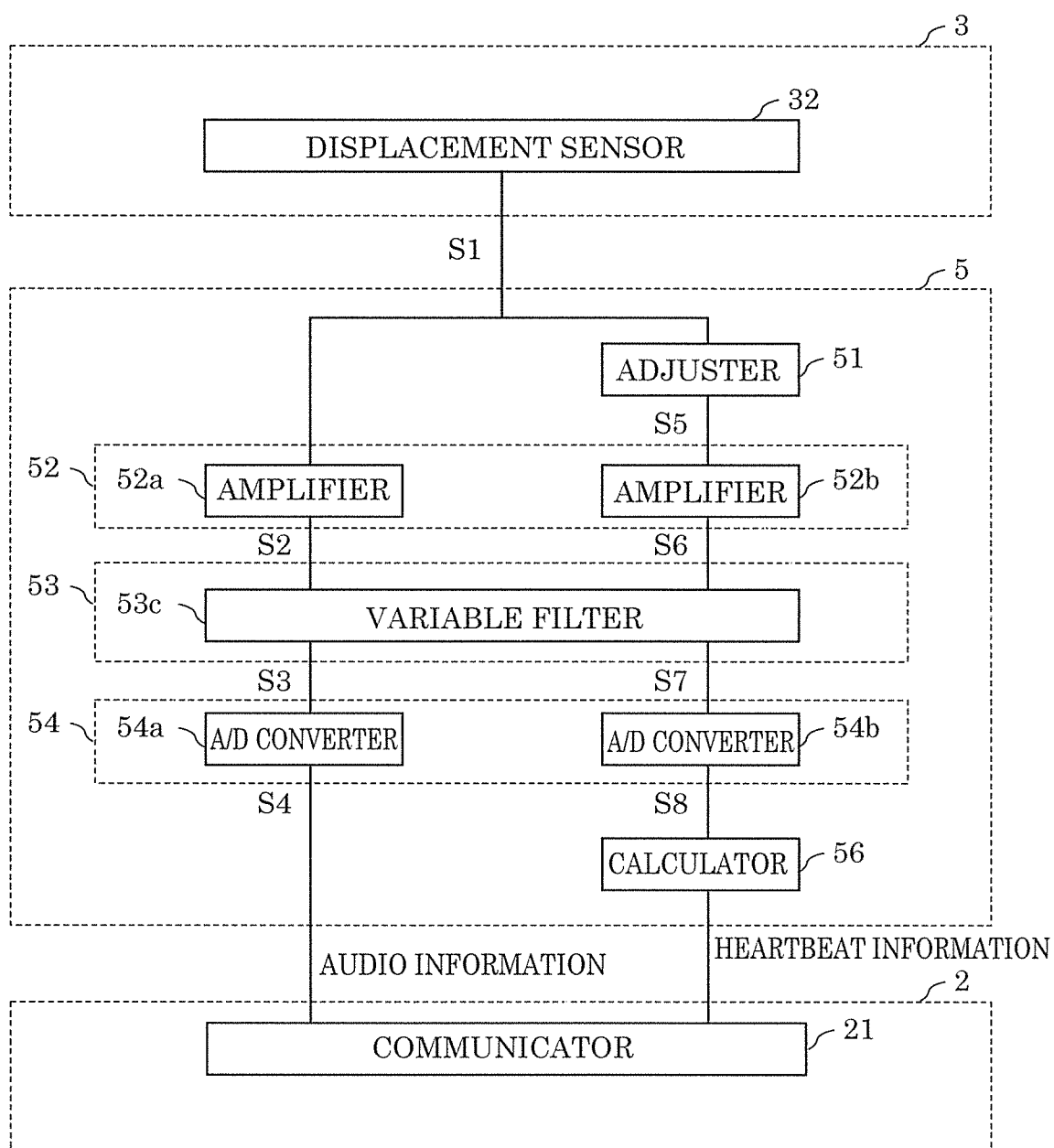
FIG. 6 is a block diagram illustrating in detail another example of a control configuration according to Embodiment 1.

It should be noted that extractor 53 may include variable filter 53c, as illustrated in FIG. 6. Variable filter 53c extracts both audio information and heartbeat information by changing a frequency bandwidth to be eliminated.

1-4. Variation 1

In Variation 1 of Embodiment 1, bone conduction microphone 3 includes amplifier 52a, audio filter 53a, and A/D converter 54a. Displacement sensor 32 in bone conduction microphone 3 converts, into signal S1, displacement on the body surface of user U in the thickness direction of the body, and outputs signal S1, as described in Embodiment 1. Amplifier 52a amplifies signal S1 and outputs signal S2 that has been amplified. Audio filter 53a extracts a frequency component that is based on audio information and is included in signal S2, and outputs signal S3. A/D converter 54a converts an analog signal into a digital signal, and outputs signal S4. Bone conduction microphone 3 transmits signal S4 which is digital data to an external device via communicator 21. In addition, bone conduction microphone 3 also outputs signal S1 to controller 5. Controller 5 includes amplifier 52b, heartbeat filter 53b, and A/D converter 54b, and extracts heartbeat information based on signal S1.

1-5. Variation 2

Figure 7:
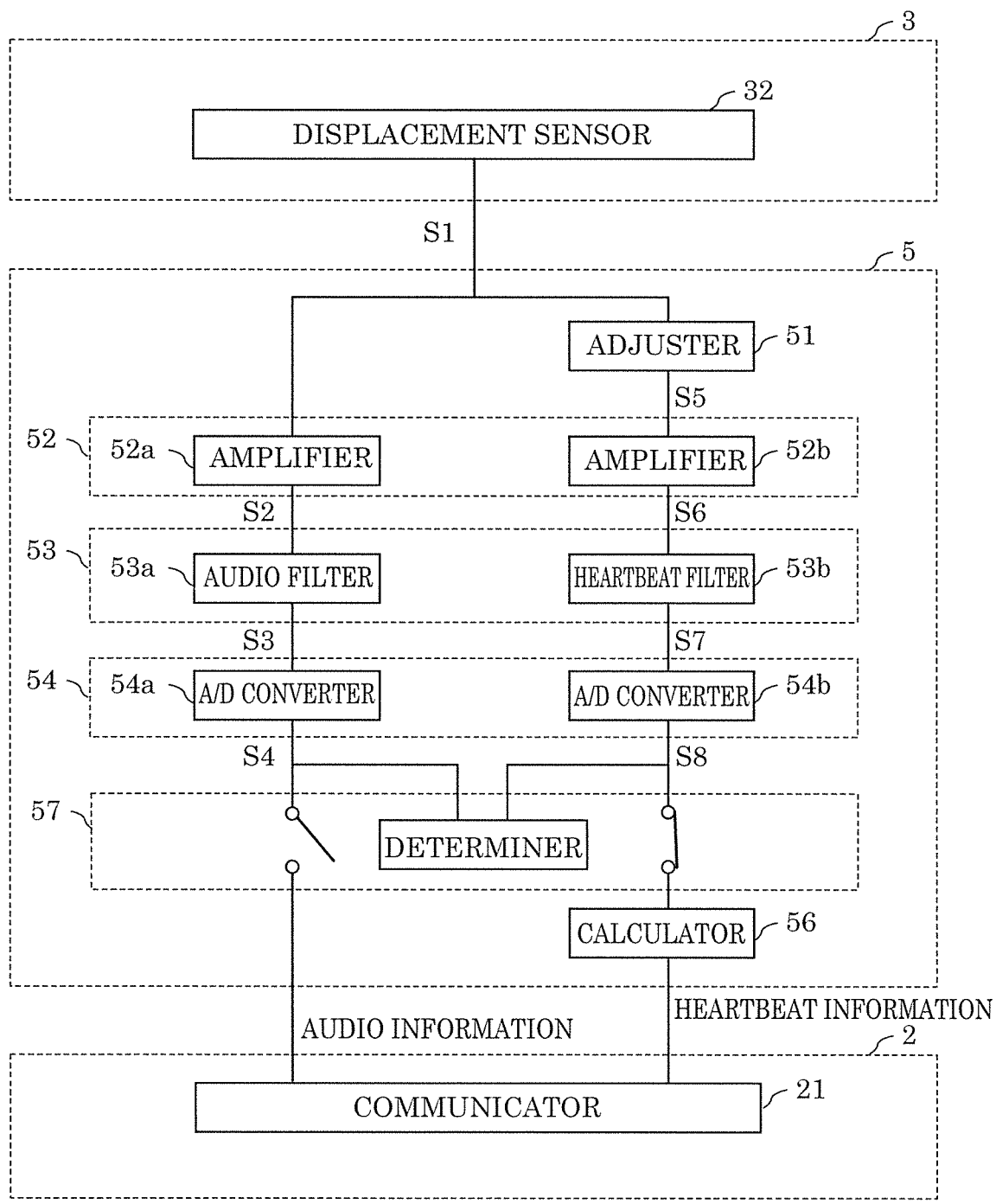
FIG. 7 is a block diagram illustrating in detail a control configuration according to Variation 2 of Embodiment 1.

FIG. 7 is a block diagram illustrating in detail a control configuration according to Variation 2 of Embodiment 1.

Heartbeat detection device 1 according to Variation 2 includes determiner 57 that determines whether signal S1 obtained by displacement sensor 32 includes audio information. As illustrated in FIG. 7, when signal S1 includes audio information, controller 5 outputs the audio information to communicator 21, and when signal S1 does not include audio information, controller 5 outputs signal S8 to calculator 56. Accordingly, calculator 56 calculates heartbeat information based on the signal that does not include audio information and it therefore becomes easier to extract the heartbeat information with accuracy.

Determiner 57 may make a determination according to the signal level of signal S1, but when determiner 57 is configured by an analog circuit, errors might occur in the signal level as affected by the degradation or temperature characteristics of a circuit element, etc. In view of this, determiner 57 makes a determination according to the signal level of a signal (signal S4 in the case where audio information has been extracted, and signal S8 in the case where heartbeat information has been extracted) that is output by A/D converter 54 in this embodiment. The signal level of audio information is higher than that of heartbeat information. This is why the signal level of a signal that includes audio information is higher than that of a signal that does not include audio information. Accordingly, when the signal level of a signal that has been output by A/D converter 54 is higher than or equal to a predetermined value, determiner 57 determines that signal S1 includes audio information, and when the signal level of the signal that has been output by A/D converter 54 is lower than the predetermined value, determines that signal S1 does not include audio information. The predetermined value may be determined for each of audio information and heartbeat information.

It should be noted that determiner 57 may make a determination according to the signal level of a signal extracted by extractor 53 (signal S3 in the case where audio information has been extracted, and signal S7 in the case where heartbeat information has been extracted), but errors might occur in the signal level due to the analog circuit configuration.

Note that bone conduction microphone 3 may include determiner 57. Determiner 57 may determine whether signal S1 includes audio information, based, for example, on the strength of pressure applied to displacement sensor 32, instead of the signal level of a signal.

Note that A/D converter 54 may include A/D converter 54c, and A/D converter 54c may convert either signal S3 or signal S7 into a digital signal based on the determination made by determiner 57. By thus using A/D converter 54c for both audio information and heartbeat information, it is possible to reduce the number of A/D converters required for controller 5. This enables lowering the cost of controller 5. Alternatively, other function(s) can be added to controller 5. In the case where it is A/D converter 54c that receives an input of signal S3, A/D converter 54c outputs signal S3 to communicator 21. In the case where it is A/D converter 54c that receives an input of signal S7, A/D converter 54c outputs signal S7 to communicator 21 via calculator 56.

1-6. Variation 3

Figure 8:
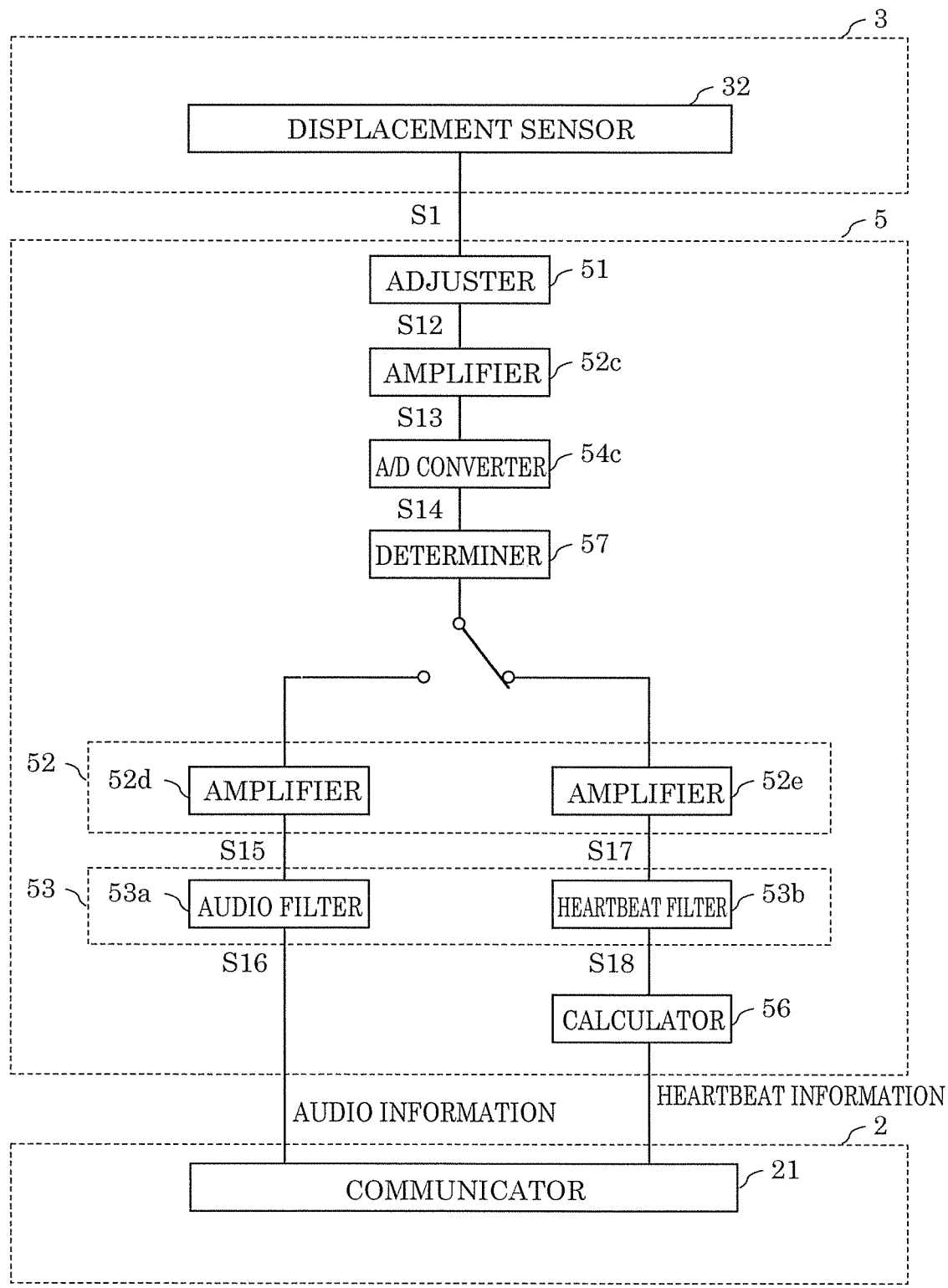
FIG. 8 is a block diagram illustrating in detail a control configuration according to Variation 3 of Embodiment 1.

FIG. 8 is a block diagram illustrating in detail a control configuration according to Variation 3 of Embodiment 1. FIG. 8 illustrates another example of a control configuration for extracting audio information and heartbeat information using determiner 57. In this variation, determiner 57 is configured by a digital circuit. This variation differs from Variation 2 in that controller 5 includes amplifiers 52c, 52d, and 52e.

First, adjuster 51 receives an input of signal S1 that is analog data and is output by displacement sensor 32, eliminates the DC offset of signal S1, adjusts the output position of signal S1, and outputs signal S12 whose output position has been adjusted. Amplifier 52c amplifies signal S12 and outputs signal S13 that has been amplified. The amplification factor of amplifier 52c may be a value between a magnification for the extraction of audio information and a magnification for the extraction of heartbeat information, e.g., an average value.

A/D converter 54 converts signal S13 that is analog data into signal S14 that is digital data.

Either audio information or heartbeat information is extracted based on the determination made by determiner 57. The determination of determiner 57 is made based on signal S14 output by A/D converter 54. Alternatively, the determination of determiner 57 may be made based on signal S16 or signal S18 extracted by extractor 53.

When audio information is extracted, amplifier 52d amplifies signal S14 so that signal S14 has amplitude appropriate for the extraction of the audio information, and outputs signal S15. When audio information is extracted, audio filter 53a extracts the audio information from signal S15 and outputs signal S16 to communicator 21.

When heartbeat information is extracted, amplifier 52e amplifies signal S14 so that signal S14 has amplitude appropriate for the extraction of the heartbeat information, and outputs signal S17. Heartbeat filter 53b extracts the heartbeat information from signal S17 and outputs signal S18 to communicator 21 via calculator 56.

1-7. Advantageous Effects, Etc.

According to this embodiment, heartbeat detection device 1 includes: bone conduction microphone 3 that converts, into signal S1, displacement on the body surface of user U in a thickness direction of the body of user U; and extractor 53 that extracts a first frequency component and a second frequency component which are included in signal S1. The first frequency component is based on audio information of user U, and the second frequency component is based on heartbeat information of user U. Thus, heartbeat detection device 1 extracts both the audio information and the heartbeat information from signal S1 that has been output by bone conduction microphone 3. User U does not need to carry plural sensors on the body, and this imposes fewer burdens on user U. In addition, it is possible to estimate the physical and psychological state of user U based on heartbeat information.

In this embodiment, bone conduction microphone 3 also includes displacement sensor 32 that converts displacement on the body surface of user U into signal S1. It is desirable that displacement sensor 32 be a piezoelectric element. With this, it is easier to obtain a signal from which both heartbeat information and audio information are extractable. Accordingly, it is easier to extract heartbeat information from a signal in which the heartbeat information and audio information overlap with each other.

In this embodiment, bone conduction microphone 3 also includes contacting component 31 via which the displacement on the body surface of user U is obtained and transmitted to displacement sensor 32. Contacting component 31 has an elastic body softer than casing 33. With this, since displacement sensor 32 is held by casing 33 via contacting component 31 that is soft, it becomes difficult to enter displacement sensor 32 for both vibration noise transmitted to casing 33 from outside and vibration noise caused inside casing 33. This allows bone conduction microphone 3 to obtain audio information and heartbeat information that propagate inside a body.

In this embodiment, extractor 53 is capable of extracting a frequency component (the second frequency component) that is based on heartbeat information and is overlapped by a frequency component (the first frequency component) that is based on audio information. This enables the extraction of heartbeat information regardless of the presence/absence of utterances.

In this embodiment, it is desirable that bone conduction microphone 3 be placed in contact with the body surface of user U such that at least part of bone conduction microphone 3 contacts a portion of the body surface above a carotid artery. This enables bone conduction microphone 3 to easily obtain heartbeat information that has higher position dependency than audio information. Accordingly, just by user's carrying one sensor on the body, it is possible to detect both audio information and heartbeat information.

In this embodiment, mounting fixture 12 of heartbeat detection device 1 causes (obtainer 30 included in) bone conduction microphone 3 to press against a predetermined portion of the body surface of user U. This reduces the risk of changing the position at which bone conduction microphone 3 is placed, and thus stabilizes the signal level of an obtained signal.

In this embodiment, bone conduction microphone 3 presses against the predetermined portion with pressure greater than or equal to 200 gram-force. With this, bone conduction microphone 3 and the body surface of user U come into a thorough contact with each other, and bone conduction microphone 3 is capable of obtaining audio information and heartbeat information that are extractable.

In this embodiment, bone conduction microphone 3 presses against the predetermined portion with pressure less than or equal to 500 gram-force. With this, an SN ratio between heartbeat information and noise that includes audio information is improved, and bone conduction microphone 3 is capable of obtaining heartbeat information that is extractable. In addition, uncomfortable feeling of user U is reduced.

According to Variation 2 of this embodiment, heartbeat detection device 1 includes determiner 57 that determines whether signal S1 obtained by displacement sensor 32 includes audio information. Based on the determination made by determiner 57, extractor 53 extracts either audio information or heartbeat information. With this, since heartbeat information is extracted based on a signal that does not include audio information, it becomes easier to extract the heartbeat information.

In this embodiment, heartbeat detection device 1 includes adjuster 51 that adjusts the output position of signal S1 at which signal S1 is output. This eliminates the influence caused, for example, by a difference brought by bone conduction microphones 3 to be used and the surrounding environment of bone conduction microphone 3. Moreover, it becomes easier to extract heartbeat information having a low signal level.

In this embodiment, controller 5 in heartbeat detection device 1 includes calculator 56 that calculates a cardiac cycle of user U based on the heartbeat information extracted by extractor 53. With this, it is possible to know the stressful state of user U.

Embodiment 2

According to heartbeat detection device 1A in Embodiment 2, displacement sensor 32 in bone conduction microphone 3 obtains displacement on the body surface of user U and converts the displacement into signal S1. Communicator 21 transmits signal S1 to heartbeat detection device 1B. Heartbeat detection device 1B extracts audio information and heartbeat information that are included in signal S1. It should be noted that the description of the same configuration as described in Embodiment 1 is omitted.

2-1. Configuration of Heartbeat Detection Device 1A

Figure 9:
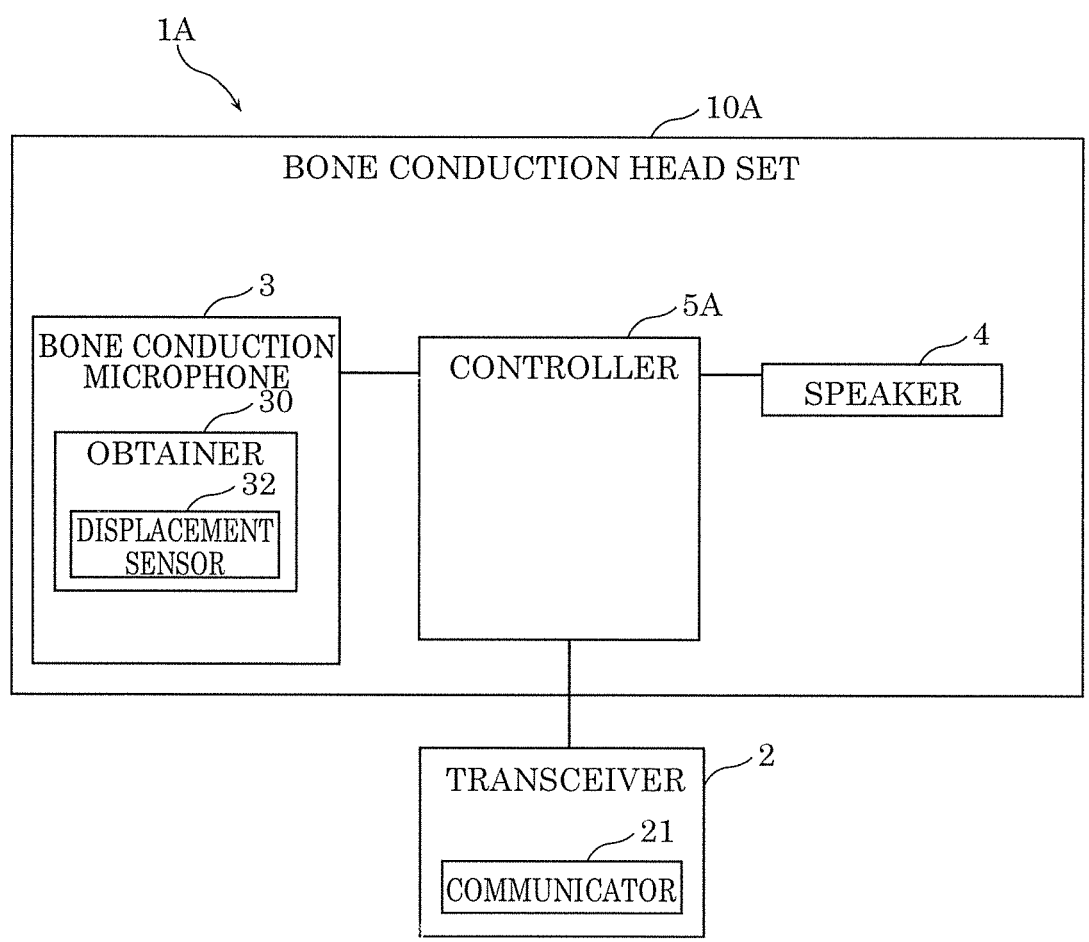
FIG. 9 is a schematic view illustrating a control configuration of a heartbeat detection device according to Embodiment 2.
Figure 10:
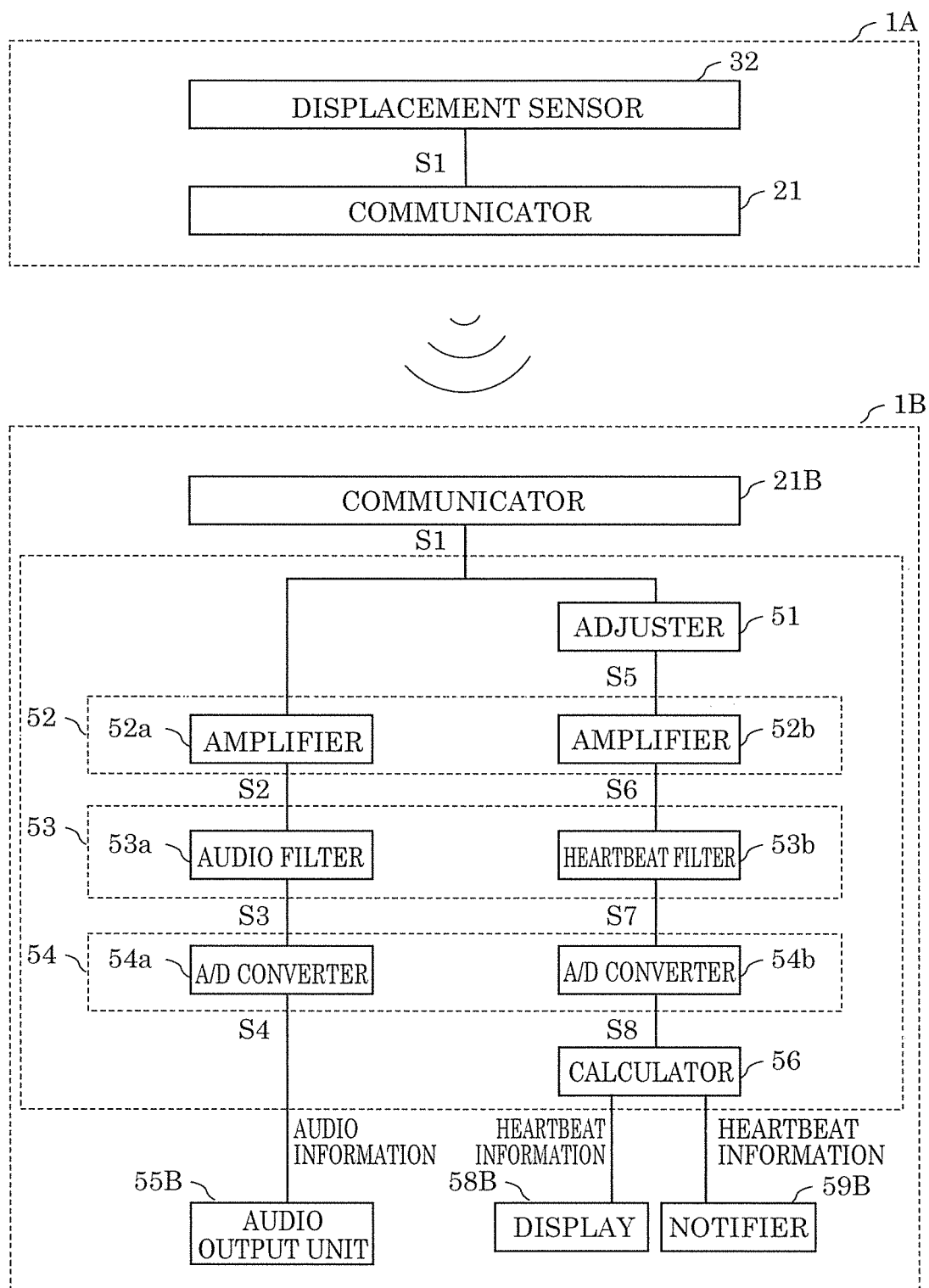
FIG. 10 is a block diagram illustrating in detail the control configuration according to Embodiment 2.

FIG. 9 is a schematic view illustrating a control configuration of heartbeat detection device 1A according to Embodiment 2. FIG. 10 is a block diagram illustrating in detail the control configuration according to Embodiment 2.

As illustrated in FIG. 9, heartbeat detection device 1A according to Embodiment 2 includes bone conduction head set 10A and transceiver 2.

Displacement sensor 32 in bone conduction microphone 3 converts displacement detected on the body surface of user U in the Z direction. Bone conduction microphone 3 outputs signal S1 to transceiver 2 via controller 5A. Communicator 21 in transceiver 2 transmits signal S1 to heartbeat detection device 1B.

2-2. Configuration of Heartbeat Detection Device 1B

Heartbeat detection device 1B is, for example, a computer configured by a central processing unit (CPU)), a random access memory (RAM), a read only memory (ROM), etc.

It should be noted that heartbeat detection device 1B may be configured by a field-programmable gate array (FPGA), an application specific integrated circuit (ASIC), a microprocessor, an analog circuit, etc.

Heartbeat detection device 1B includes communicator 21B, controller 5B, audio output unit 55B, display 58B, and notifier 59B.

As illustrated in FIG. 10, communicator 21B receives signal S1 from communicator 21 in heartbeat detection device 1A. Controller 5B extracts audio information and heartbeat information from signal S1 received by communicator 21B. Controller 5B includes adjuster 51, amplifier 21B, extractor 53, A/D converter 54, setting unit 55, and calculator 56. Since the extraction of audio information and heartbeat information carried out by controller 5B is the same as that described in Embodiment 1, the description is omitted.

Audio output unit 55B outputs signal S4 and communicates via voice, for example, with user U.

Display 58B displays heartbeat information extracted by extractor 53 and the output of calculator 56 (e.g., data indicating cardiac cycle, heart rate, and heartbeat fluctuations). Note that display 58B may display signal S8. With this, it is possible to monitor the state of user U.

It should be noted that heartbeat detection device 1B may include notifier 59B that transmits a notification when data indicating an analysis result includes an abnormal value. Notifier 59B outputs, for example, a warning tone.

It should be noted that communicator 21B may transmit, to an external device, signal S8 indicating heartbeat information and the output of calculator 56. The external device, for example, displays or further analyzes the transmitted data.

Figure 11:
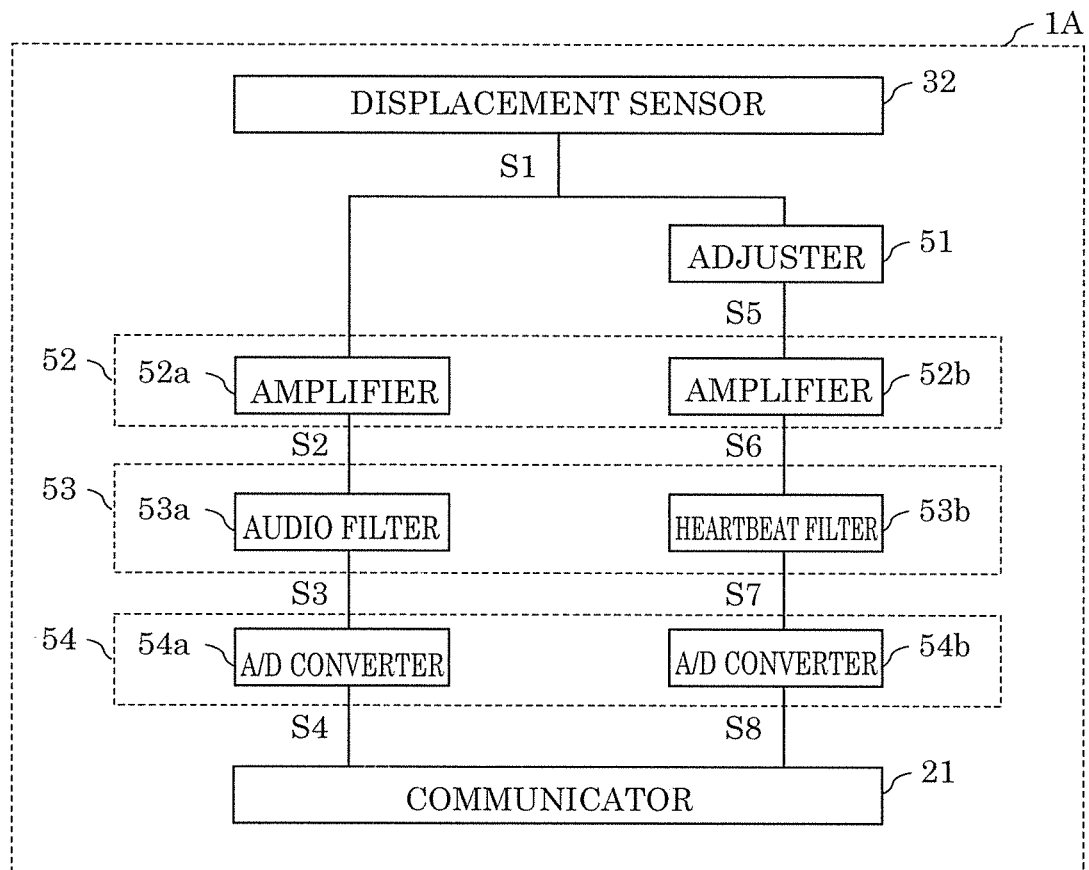
FIG. 11 is a block diagram showing in detail another example of a control configuration according to Embodiment 2.
Figure 11:
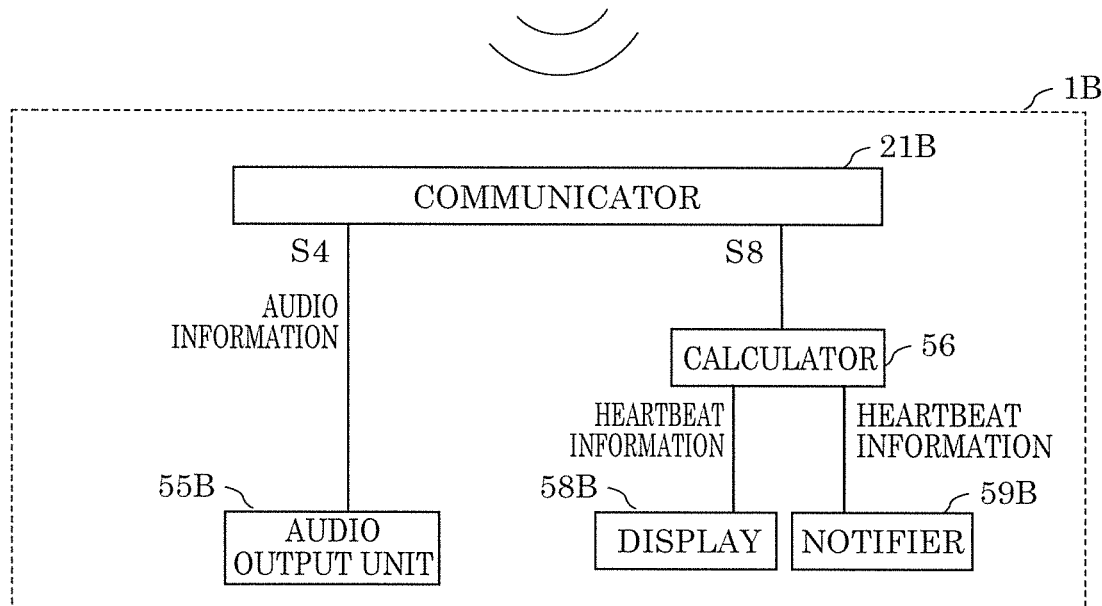

It should be noted that heartbeat detection device 1A may include amplifier 52, extractor 53, and A/D converter 54, extract audio information and heartbeat information, and transmit the extracted information to an external device via communicator 21, as illustrated in FIG. 11. Heartbeat detection device 1B receives signal S8, and performs analysis processing of the heartbeat information. Heartbeat detection device 1B may receive signal S4 transmitted by heartbeat detection device 1A and output signal S4 via audio output unit 55B.

2-3. Advantageous Effects, Etc.

In this embodiment, heartbeat detection device 1B includes: communicator 21B that receives signal S4 in which audio information and heartbeat information are included; and extractor 53 that extracts the audio information and heartbeat information included in signal S4. With this, it is possible to extract, from a signal that includes audio information and heartbeat information, the audio information and the heartbeat information. It is thus possible to estimate the state of user U based on the extracted heartbeat information.

Embodiment 3

Embodiment 3 describes in detail an example of calculator 56 in the heartbeat detection device according to Embodiment 1 or 2.

3-1. Calculation of Cardiac Cycle

Figure 12:
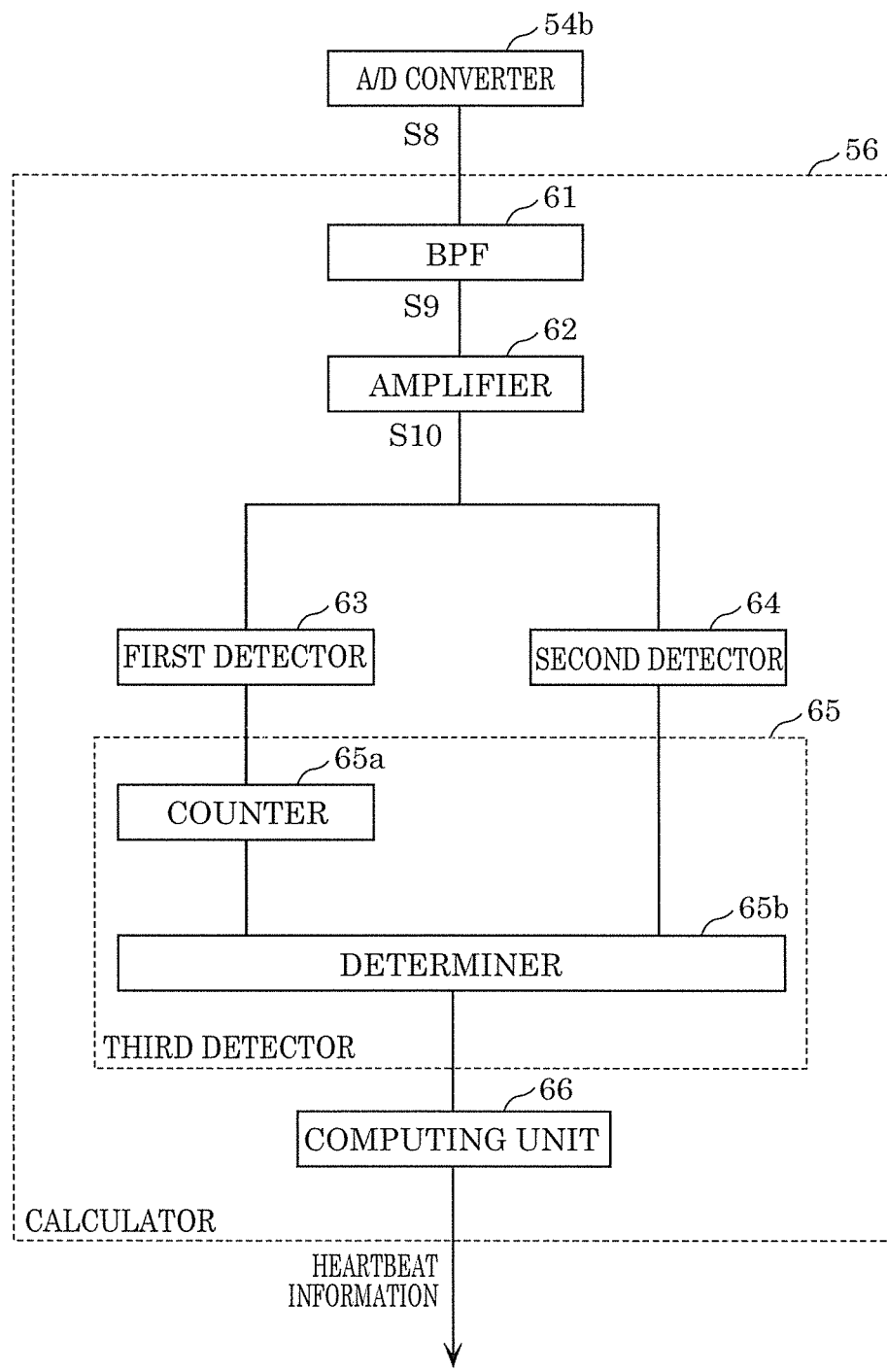
FIG. 12 is a block diagram illustrating a configuration of a calculator according to Embodiment 3.
Figure 13:
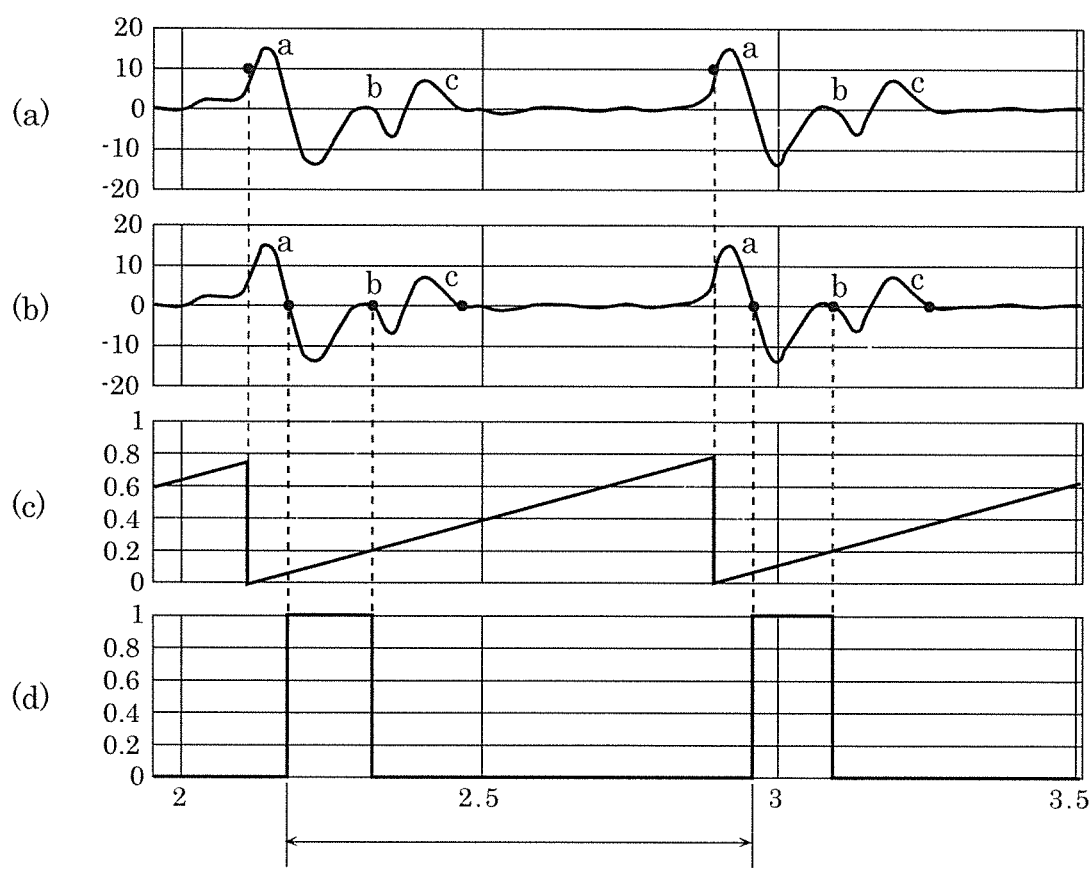
FIG. 13 is a pattern diagram illustrating waveforms output by the calculator according to Embodiment 3.

FIG. 12 is a pattern diagram illustrating a configuration of calculator 56 according to this embodiment. FIG. 13 is a block diagram illustrating waveforms that are output by calculator 56 according to this embodiment.

Calculator 56 calculates a cardiac cycle of user U based on signal S8. Signal S8 is a heartbeat signal (a signal based on heartbeat information). A heartbeat signal obtained by bone conduction microphone 3 has substantially cyclic waveforms that reflect ventricular and atrial contraction and relaxation. The waveforms each having its peak on positive potential in a heartbeat signal generated by one heartbeat are waves a, b, and c in the order of elapsed time, as illustrated in FIG. 13. Each of waves b and c has smaller amplitude than wave a.

As illustrated in FIG. 12, calculator 56 includes BPF 61, amplifier 62, first detector 63, second detector 64, third detector 65, and computing unit 66.

BPF 61 is a band pass filter that extracts a predetermined frequency bandwidth included in signal S8. An LPF in BPF 61 eliminates noises having high frequency components. An HPF in BPF 61 causes a DC component in signal S8 to accord with a zero reference value. In this embodiment, a BPF that eliminates a frequency bandwidth in the range from 1 Hz to 10 Hz is used for BPF 61.

Amplifier 62 amplifies signal S9 to signal S10 by appropriately changing an amplification factor so that the largest amplitude (amplitude of wave a) of an amplified signal indicates a predetermined value. Amplifier 62 switches from one amplification factor to another in a cycle (hereinafter referred to as "switching cycle") determined based on a cardiac cycle. A predetermined fixed value (e.g., one second) may be used for a switching cycle. Note that since a switching cycle differs from person to person, it may be appropriately set based on the cardiac cycle of user U.

First detector 63 detects a plurality of waves a included in signal S10. As illustrated in (a) in FIG. 13, first detector 63 detects a plurality of first time points at each of which signal S10 changes from a value less than the first value to a value greater than or equal to the first value. In this embodiment, the first value may be smaller than or equal to the largest value of signal S10 since the first time point is not used for the calculation of a cycle even when a waveform other than that of wave a is detected as the first time point. It is, however, desirable to set the first value to a value less than or equal to the amplitude of wave a and greater than the amplitudes of waves b and c, e.g., greater than or equal to 50 percent of the amplitude of wave a (the largest value of a heartbeat signal).

The first time point is not used as a time point for calculating a cycle, but is used to detect waves a. Accordingly, errors in terms of time are tolerated and this enables detection with less amount of calculation. It should be noted that in this embodiment, a predetermined value for determining an amplification factor of amplifier 62 is defined, as a reference for the first value, to be 100 percent of the amplitude of wave a. Since amplifier 62 feeds back the amplification factor determined based on signal S10 that has been output, and then amplifies signal S9, the amplitude of wave a might be smaller than the predetermined value.

Accordingly, the first value may be defined to be less than 100 percent of the predetermined value.

Note that the first time point may be a point in time at which signal S10 changes from a value greater than the first value to a value less than or equal to the first value.

Second detector 64 detects a plurality of points at each of which signal S10 decreases after having increased in the direction of positive potential, and indicates the second value. As illustrated in (b) in FIG. 13, second detector 64 detects a plurality of second time points at each of which signal S10 changes from a value greater than the second value to a value less than or equal to the second value. The second value is a value smaller than the first value.

Since the second time point is used as a detection point for calculating a cycle, fewer errors are required in the detection of the second time points. A heartbeat signal has the largest gradient near the center of vibration. Since adjuster 51 makes an adjustment so that the output position of a DC component in the heartbeat signal accords with a zero reference value, it is desirable that the second value be the zero reference value.

Third detector 65 detects a plurality of detection points each being a different one of the second time points which is immediately after a different one of the first time points. As illustrated in (c) in FIG. 13, counter 65a counts an elapsed time from the first time point defined as a starting point of the elapsed time. Determiner 65b determines, based on counter 65a, whether an elapsed time from a starting point to the second time point that is immediately after the starting point is less than a threshold value.

Based on the determination, determiner 65b starts or stops outputting a detection value at the second time point, as illustrated in (d) in FIG. 13. The starting point at which the output of the detection value is started is used for the calculation of a cardiac cycle. As illustrated in (d) in FIG. 13, when the elapsed time at the second time point that is immediately after the starting point is less than the threshold value, determiner 65b determines that the second time point is a detection point and starts outputting a detection value "1" indicating that the second time point is a detection point. Determiner 65b stops outputting the detection value at the following second time point (the second time point that is not immediately after the starting point). When the output of the detection value is stopped, a non-detection value shall be "0". When the elapsed time at the second time point that is immediately after the starting point is greater than or equal to the threshold value, determiner 65b determines that the second time point is not a detection point, and does not start outputting the detection value. This reduces the risk of detecting a wrong detection point.

Computing unit 66 calculates a cardiac cycle based on the intervals of the plurality of detection points detected by third detector 65.

It should be noted that in (d) in FIG. 13, determiner 65b defines a detection value as "1" and a non-detection value as "0", but the detection value and the non-detection value shall not be limited to such. Any value may be set for the detection value and the non-detection value as long as they indicate different values. Determiner 65b may output a plurality of non-detection values, e.g., outputting a value assigned to the second time point that is not immediately after the first time point, which is different from a value assigned to the second time point that is immediately after the first time point.

Note that in this embodiment, the output of a detection value is started at a detection point and is stopped at the following second time point, but a detection value may be output at a detection point and the output of the detection value may be stopped after a predetermined period of time, e.g., 0.1 seconds.

Note also that calculator 56 according to this embodiment may calculate a cardiac cycle based on signal S18 that is output by heartbeat filter 53b illustrated in FIG. 8, as described in Variation 3 of Embodiment 1.

It should be also noted that calculator 56 according to this embodiment may calculate a cardiac cycle based on a heartbeat signal obtained by a device other than a bone conduction microphone. This embodiment is especially useful for calculating a cardiac cycle with high accuracy based on more moderate signal waveforms, e.g., acceleration pulse waves, compared to those presented in an electrocardiogram.

3-2. Variation 1

Figure 14:
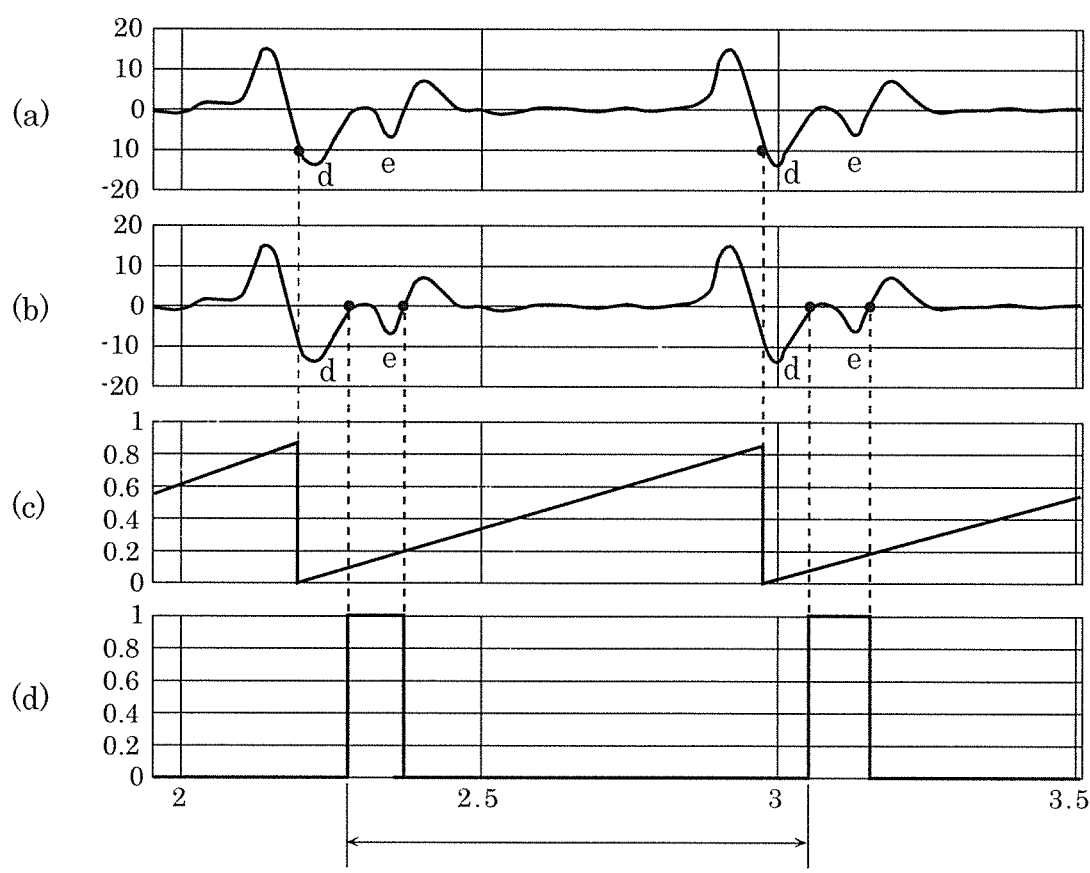
FIG. 14 is a pattern diagram illustrating waveforms output by a calculator according to Variation 1 of Embodiment 3.

FIG. 14 is a pattern diagram illustrating waveforms that are output by calculator 56 according to Variation 1 of this embodiment. The configuration of calculator 56 is the same as that illustrated in FIG. 12.

As illustrated in FIG. 14, waveforms each having its peak on negative potential in a heartbeat signal generated by one heartbeat are waves d and e in the order of elapsed time. The heartbeat signal generated by one heartbeat has, in many cases, the largest amplitude in wave d and reduces the amplitude as time elapses.

Calculator 56 calculates a cardiac cycle based on waveforms each having its peak on negative potential. Calculator 56 includes BPF 61, amplifier 62, first detector 63, second detector 64, third detector 65, and computing unit 66. Since the configurations of BPF 61 and amplifier 62 are the same as those described in Embodiment 3, the description is omitted.

First detector 63 detects waves d included in signal S10. As illustrated in (a) in FIG. 14, first detector 63 detects a plurality of third time points at each of which signal S10 changes from a value greater than the third value to a value less than or equal to the third value. The third value may be a value greater than or equal to the smallest value of signal S10. However, it is desirable that the third value is set to a value greater than or equal to the amplitude of wave d and smaller than the amplitude of wave e, e.g., a value less than or equal to 50 percent of the amplitude of wave d (the smallest value of a heartbeat signal).

Note that the third time point may be a point in time at which signal S10 changes from a value less than the third value to a value greater than or equal to the third value.

Second detector 64 detects a plurality of points to each of which a potential rises to indicate the fourth value after a waveform has been generated in negative potential. As illustrated in (b) in FIG. 14, second detector 64 detects a plurality of fourth time points at each of which signal S10 changes from a value less than the fourth value to a value greater than or equal to the fourth value. The fourth value is a value greater than the third value. In this embodiment, the fourth value is defined as a zero reference value.

Third detector 65 detects a plurality of detection points each being a different one of the fourth time points which is immediately after a different one of the third time points.

As illustrated in (c) in FIG. 14, counter 65a counts an elapsed time from the third time point defined as a starting point of the elapsed time.

Determiner 65b determines, based on counter 65a, whether an elapsed time from a starting point to the fourth time point that is immediately after the starting point is less than a threshold value. Based on the determination, determiner 65b starts or stops the output of a detection value at the fourth time point, as illustrated in (d) in FIG. 14. Since the start and stop of the output carried out by determiner 65b is the same as those performed by determiner 65b in Embodiment 3, the description is omitted.

Computing unit 66 calculates a cardiac cycle based on the intervals of the plurality of detection points detected by third detector 65.

It should be noted that when the electric potential of a heartbeat signal is inverted, it is possible for calculator 56 to calculate a cardiac cycle by assuming wave a illustrated in FIG. 13 to be wave d according to this variation.

3-3. Variation 2

Figure 15:
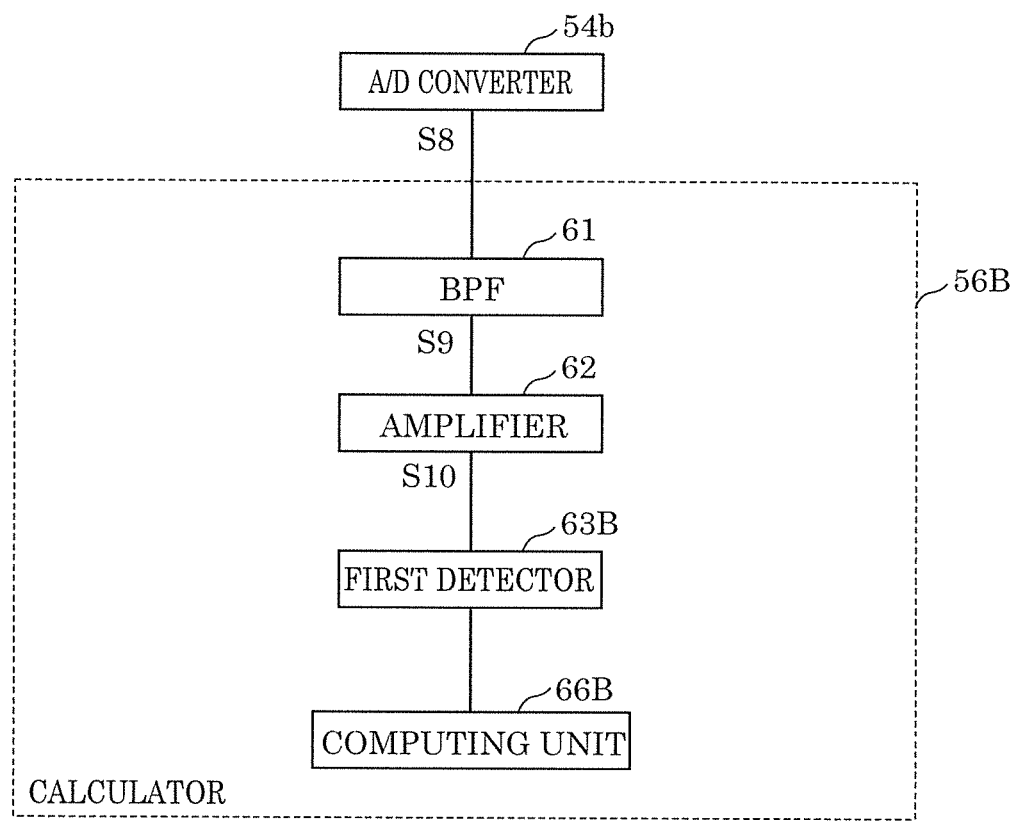
FIG. 15 is a block diagram illustrating a configuration of a calculator according to Variation 2 of Embodiment 3.
Figure 16:
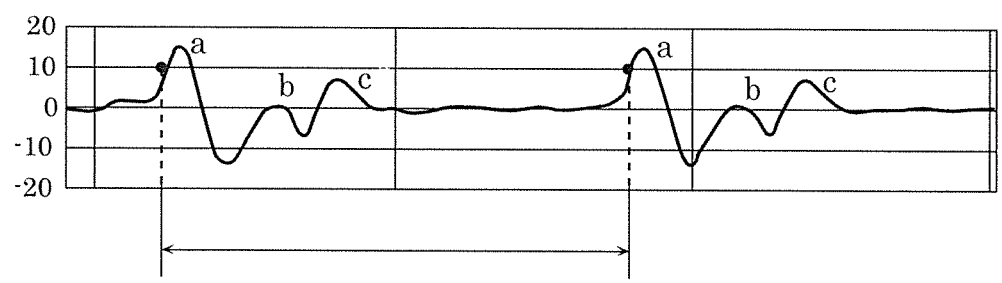
FIG. 16 is a pattern diagram illustrating waveforms output by the calculator according to Variation 2 of Embodiment 3.

FIG. 15 is a block diagram illustrating a configuration of calculator 56 according to Variation 2 of this embodiment. FIG. 16 is a pattern diagram illustrating waveforms that are output by calculator 56B according to Variation 2 of this embodiment.

Calculator 56B includes BPF 61, amplifier 62, first detector 63B, and computing unit 66B. Since the configurations of BPF 61 and amplifier 62 are the same as those described in Embodiment 3, the description is omitted.

First detector 63B detects waves a included in signal S10. As illustrated in FIG. 16, first detector 66B detects a plurality of fifth time points at each of which signal S10 changes from a value less than the fifth value to a value greater than or equal to the fifth value. The fifth value is a value less than or equal to the amplitude of wave a and greater than the amplitudes of waves b and c. In this embodiment, the fifth value is defined to be less than 90 percent of the amplitude of wave a (the largest value of a heartbeat signal). Note that the fifth time point may be a point in time at which signal S10 changes from a value greater than the fifth value to a value less than or equal to the fifth value.

The waveforms of a heartbeat signal obtained by bone conduction microphone 3 each have a smaller gradient near its peak compared to waveforms obtained in an electrocardiogram, and thereby, errors might occur when the first value is set to a large value for detecting peak points. Accordingly, for the fifth value used as a detection point, a value in a part where the gradient of wave a is large, e.g., a value less than 90 percent of the amplitude of wave a, is used.

It should be noted that the fifth value may be a value less than or equal to the amplitude of wave a and greater than the amplitudes of waves b and c, e.g., a value greater than or equal to 50 percent of the amplitude of wave a. With this, it is possible to enhance the accuracy of a cardiac cycle.

Computing unit 66B calculates a cardiac cycle based on the intervals of the plurality of fifth time points.

3-4. Advantageous Effects, Etc.

According to this embodiment, heartbeat detection device 1 receives an input of a heartbeat signal of user U, and includes: first detector 63 that detects a plurality of first time points each being one of: a point in time at which the heartbeat signal changes from a value less than a first value to a value greater than or equal to the first value; and a point in time at which the heartbeat signal changes from a value greater than the first value to a value less than or equal to the first value; second detector 64 that detects a plurality of second time points each being a point in time at which the heartbeat signal changes from a value greater than a second value to a value less than or equal to the second value, the second value being smaller than the first value; third detector 65 that detects a plurality of detection points each being a different one of the plurality of second time points which is immediately after a different one of the plurality of first time points; and computing unit 66 that calculates a cardiac cycle of user U based on intervals of the plurality of detection points. With this, heartbeat detection device 1 is capable of calculating a cardiac cycle based on detection points detected with fewer errors in terms of time.

According to this embodiment, the second value used by second detector 64 for the detection of the second time points is a zero reference value. With this, a heartbeat signal has a larger gradient near the second value, and this reduces errors in terms of time in the detection of the second time points.

According to this embodiment, third extractor 65 includes: counter 65a that counts an elapsed time from each of the plurality of first time points which is defined as a starting point; and determiner 65b that: determines that, when the elapsed time at each of the plurality of second time points which is immediately after the starting point is less than a threshold value, the second time point is a detection point included in the plurality of detection points; and determines that, when the elapsed time at each of the second time points is greater than or equal to the threshold value, the second time point is not the detection point. This reduces the risk of erroneously detecting, as a detection point, a moderate waveform (e.g., wave c) generated in the latter period of an elapsed time.

According to this embodiment, determiner 65b starts outputting a detection value when the elapsed time is less than the threshold value at each of the plurality of second time points which is immediately after the starting point of the counting of the elapsed time by counter 65a, and stops outputting the detection value at each of the plurality of second time points which is not immediately after the starting point. Computing unit 66 defines, as a detection point, a point in time at which determiner 65b has started outputting the detection value, and thus calculates a cardiac cycle. This reduces the risk of erroneously detecting the component of wave b as a detection point when first detector 63 detects wave b by mistake in the detection of a detection point.

According to this embodiment, heartbeat detection device 1 includes adjuster 51 that adjusts an output position at which a heartbeat signal is output. With this, values in a larger gradient of a heartbeat signal approximate a zero reference value, and this reduces errors in terms of time when a constant value is applied to the second value.

According to this embodiment, heartbeat detection device 1 includes amplifier 62 that amplifies a heartbeat signal so that the largest amplitude of the heartbeat signal indicates a predetermined value. Thus, it is possible to set the first value by using, as a reference for the setting, a predetermined value for determining an amplification factor of amplifier 62, and this enhances accuracy in the detection of the first value in wave a.

According to Variation 1 of this embodiment, heartbeat detection device 1 receives an input of a heartbeat signal indicating a change in waveforms that vary based on the heartbeats of user U, and includes: first detector 63 that detects a plurality of third time points each being one of: a point in time at which the heartbeat signal changes from a value less than a third value to a value greater than or equal to the third value; and a point in time at which the heartbeat signal changes from a value greater than the third value to a value less than or equal to the third value; and second detector 64 that detects a plurality of fourth time points each being a point in time at which the heartbeat signal changes from a value less than a fourth value to a value greater than or equal to the fourth value, the fourth value being greater than the third value; third detector 65 that detects a plurality of detection points each being a different one of the plurality of the fourth time points which is immediately after a different one of the plurality of third time points; and computing unit 66 that calculates a cardiac cycle of the user based on intervals of the plurality of detection points. With this, it is possible to calculate a cardiac cycle based on the waveforms of a heartbeat signal, each of which has its peak on negative potential.

According to Variation 2 of this embodiment, heartbeat detection device 1 receives an input of a heartbeat signal indicating a change in waveforms that vary based on the heartbeats of user U, and includes: first detector 63B that detects a plurality of fifth time points each being one of: a point in time at which the heartbeat signal changes from a value less than a fifth value to a value greater than or equal to the fifth value; and a point in time at which the heartbeat signal changes from a value greater than the fifth value to a value less than or equal to the fifth value, the fifth value being less than 90 percent of a largest value of the heartbeat signal; and computing unit 66B that calculates a cardiac cycle of user U based on intervals of the plurality of fifth time points. With this, it is possible to easily calculate a cardiac cycle with high accuracy.

Although only some exemplary embodiments of the present disclosure have been described in detail above, those skilled in the art will readily appreciate that many modifications are possible in the exemplary embodiments without materially departing from the novel teachings and advantages of the present disclosure. Accordingly, all such modifications are intended to be included within the scope of the present disclosure.

INDUSTRIAL APPLICABILITY

The present disclosure is applicable to a sound collection device placed in contact with a human body to obtain audio information. The present disclosure is also applicable to an audio input/output device in the case of wearing a helmet used at a place such as a construction site, a factory, or a distribution warehouse, a motorcycle helmet, a headphone, or an intercommunication device, and thus communicating via voice with a person on the other end of the communication.

What is claimed is:

1. A heartbeat detection device, comprising:
    a bone conduction microphone that converts, into a first signal, displacement on a body surface of a user in a thickness direction of a body of the user;
    an extractor that includes an audio filter and a heartbeat filter and extracts (i) a first frequency component using the audio filter and (ii) a second frequency component using the heartbeat filter, the audio filter passing an audio frequency component, the heartbeat filter passing a heartbeat frequency component, the first frequency component being included in the first signal and based on audio information of the user, the second frequency component being included in the first signal and based on heartbeat information of the user; and
    a mounting fixture that causes the bone conduction microphone to press against the body surface of the user,
    wherein the bone conduction microphone presses against the body surface of the user with pressure greater than or equal to 200 gram-force.

2. The heartbeat detection device according to claim 1, wherein
    the bone conduction microphone includes a piezoelectric element that converts the displacement into the first signal.

3. The heartbeat detection device according to claim 2, wherein
    the bone conduction microphone includes an elastic body via which the displacement is obtained and transmitted to the piezoelectric element.

4. The heartbeat detection device according to claim 1, wherein
    the first signal includes the first frequency component and the second frequency component which overlap with each other.

5. The heartbeat detection device according to claim 4, wherein
    the extractor extracts the second frequency component overlapped with the first frequency component.

6. The heartbeat detection device according to claim 1, wherein
    the bone conduction microphone is placed in contact with the body surface of the user such that at least part of the bone conduction microphone contacts a portion of the body surface above a carotid artery.

7. The heartbeat detection device according to claim 1, wherein the extractor includes:
    a first extractor that extracts the first frequency component; and
    a second extractor that extracts the second frequency component.

8. The heartbeat detection device according to claim 1, further comprising:
    an adjuster that adjusts an output position at which the first signal is output.

9. The heartbeat detection device according to claim 1, further comprising:
    a calculator that calculates a cardiac cycle of the user based on the second frequency component extracted by the extractor.

10. A heartbeat detection device, comprising:
    a bone conduction microphone that converts, into a first signal, displacement on a body surface of a user in a thickness direction of a body of the user;
    an extractor that includes an audio filter and a heartbeat filter and extracts (i) a first frequency component using the audio filter and (ii) a second frequency component using the heartbeat filter, the audio filter passing an audio frequency component, the heartbeat filter passing a heartbeat frequency component, the first frequency component being included in the first signal and based on audio information of the user, the second frequency component being included in the first signal and based on heartbeat information of the user; and
    a mounting fixture that causes the bone conduction microphone to press against the body surface of the user,
    wherein the bone conduction microphone presses against the body surface of the user with pressure less than or equal to 500 gram-force.

11. A heartbeat detection device, comprising:
    a bone conduction microphone that converts, into a first signal, displacement on a body surface of a user in a thickness direction of a body of the user;

an extractor that includes an audio filter and a heartbeat filter and extracts (i) a first frequency component using the audio filter and (ii) a second frequency component using the heartbeat filter, the audio filter passing an audio frequency component, the heartbeat filter passing a heartbeat frequency component, the first frequency component being included in the first signal and based on audio information of the user, the second frequency component being included in the first signal and based on heartbeat information of the user;

a first detector that detects a plurality of first time points each being one of (i) a point in time at which the second frequency component changes from a value less than a first value to a value greater than or equal to the first value, and (ii) a point in time at which the second frequency component changes from a value greater than the first value to a value less than or equal to the first value;

a second detector that detects a plurality of second time points each being a point in time at which the second frequency component changes from a value greater than a second value to a value less than or equal to the second value, the second value being smaller than the first value;

a third detector that detects a plurality of detection points each being a different one of the plurality of second time points which is immediately after a different one of the plurality of first time points; and a computing unit that calculates a cardiac cycle of the user based on intervals of the plurality of detection points.

12. The heartbeat detection device according to claim 11, wherein the third extractor includes:
  a counter that counts an elapsed time from each of the plurality of first time points which is defined as a starting point; and
  a determiner that
    determines that, when the elapsed time at each of the second time points which is immediately after the starting point is less than a threshold value, the second time point is a detection point included in the plurality of detection points; and
    determines that, when the elapsed time at each of the plurality of second time points is greater than or equal to the threshold value, the second time point is not the detection point.

13. The heartbeat detection device according to claim 12, wherein the computing unit defines, as the detection point, a point in time at which the determiner has started outputting a detection value, and the determiner:
  starts outputting the detection value when the elapsed time at each of the plurality of second time points which is immediately after the starting point is less than the threshold value, and stops outputting the detection value at each of the plurality of second time points which is not immediately after the starting point; and
  does not start outputting the detection value when the elapsed time at each of the plurality of second time points is greater than or equal to the threshold value.

14. A heartbeat detection device, comprising:

a bone conduction microphone that converts, into a first signal, displacement on a body surface of a user in a thickness direction of a body of the user;

an extractor that includes an audio filter and a heartbeat filter and extracts (i) a first frequency component using the audio filter and (ii) a second frequency component using the heartbeat filter, the audio filter passing an audio frequency component, the heartbeat filter passing a heartbeat frequency component, the first frequency component being included in the first signal and based on audio information of the user, the second frequency component being included in the first signal and based on heartbeat information of the user;

a first detector that detects a plurality of first time points each being one of (i) a point in time at which the second frequency component changes from a value less than a third value to a value greater than or equal to the third value, and (ii) a point in time at which the second frequency component changes from a value greater than the third value to a value less than or equal to the third value;

a second detector that detects a plurality of second time points each being a point in time at which the second frequency component changes from a value less than a fourth value to a value greater than or equal to the fourth value, the fourth value being greater than the third value;

a third detector that detects a plurality of detection points each being a different one of the plurality of second time points which is immediately after a different one of the plurality of first time points; and a computing unit that calculates a cardiac cycle of the user based on intervals of the plurality of detection points.

15. A heartbeat detection device, comprising:

a bone conduction microphone that converts, into a first signal, displacement on a body surface of a user in a thickness direction of a body of the user;

an extractor that includes an audio filter and a heartbeat filter and extracts (i) a first frequency component using the audio filter and (ii) a second frequency component using the heartbeat filter, the audio filter passing an audio frequency component, the heartbeat filter passing a heartbeat frequency component, the first frequency component being included in the first signal and based on audio information of the user, the second frequency component being included in the first signal and based on heartbeat information of the user;

a first detector that detects a plurality of first time points each being one of (i) a point in time at which the frequency component changes from a value less than a fifth value to a value greater than or equal to the fifth value, and (ii) a point in time at which the second frequency component changes from a value greater than the fifth value to a value less than or equal to the fifth value, the fifth value being less than 90 percent of a largest value of the second frequency component; and a computing unit that calculates a cardiac cycle of the user based on intervals of the plurality of first time points.

16. A heartbeat detection method, comprising:

placing a bone conduction microphone in contact with a surface body of a user;

converting, into a first signal, displacement on the body surface in a thickness direction of a body of the user;

extracting (i) a first frequency component using an audio filter that passes an audio frequency component and (ii) a second frequency component using a heartbeat filter that passes a heartbeat frequency component, the first frequency component being included in the first signal and based on audio information of the user, the second frequency component being included in the first signal and based on heartbeat information of the user;

detecting a first time point which is one of (i) a point in time at which the second frequency component changes from a value less than a first value to a value greater than or equal to the first value, and (ii) a point in time at which the second frequency component changes from a value greater than the first value to a value less than or equal to the first value;

detecting a second time point which is a point in time at which the second frequency component changes from a value greater than a second value to a value less than or equal to the second value, the second value being smaller than the first value;

detecting a detection point which is the second time point that is immediately after the first time point; and detecting a plurality of detection points each being the detection point, by repeating the detecting of the first time point, the detecting of the second time point, and the detecting of the detection point, and subsequently calculating a cardiac cycle of the user based on intervals of the plurality of detection points.

* * * * *